(12) United States Patent
Boveja

(10) Patent No.: US 6,879,859 B1
(45) Date of Patent: *Apr. 12, 2005

(54) EXTERNAL PULSE GENERATOR FOR ADJUNCT (ADD-ON) TREATMENT OF OBESITY, EATING DISORDERS, NEUROLOGICAL, NEUROPSYCHIATRIC, AND UROLOGICAL DISORDERS

(76) Inventor: Birinder R. Boveja, P.O. Box 210095, Milwaukee, WI (US) 53221

( * ) Notice: Subject to any disclaimer, the term of this patent is extended or adjusted under 35 U.S.C. 154(b) by 271 days.

This patent is subject to a terminal disclaimer.

(21) Appl. No.: 10/079,215

(22) Filed: Feb. 20, 2002

Related U.S. Application Data

(63) Continuation-in-part of application No. 09/751,966, filed on Dec. 29, 2000, now Pat. No. 6,366,814, which is a continuation-in-part of application No. 09/178,060, filed on Oct. 26, 1998, now Pat. No. 6,205,359.

(51) Int. Cl.[7] .............................................. A61N 1/18
(52) U.S. Cl. ........................................ 607/45; 607/58
(58) Field of Search ............................. 607/40, 41, 45, 607/46, 58, 59, 61, 63, 66, 72, 116, 118, 120

(56) References Cited

U.S. PATENT DOCUMENTS

| | | | |
|---|---|---|---|
| 3,760,812 A | 9/1973 | Timm et al. ................ | 128/418 |
| 3,796,221 A | 3/1974 | Hagfors et al. ............ | 128/421 |
| 4,573,481 A | 3/1986 | Bullara ...................... | 128/784 |
| 4,702,254 A | 10/1987 | Zabara et al. ............... | 128/421 |
| 4,867,164 A | 9/1989 | Zabara et al. ............... | 128/421 |
| 5,025,807 A | 6/1991 | Zabara et al. ............... | 128/421 |
| 5,299,569 A | 4/1994 | Wernicke et al. .......... | 607/118 |
| 5,304,206 A | 4/1994 | Baker et al. .................. | 607/2 |
| 5,540,734 A * | 7/1996 | Zabara ........................ | 607/46 |
| 6,205,359 B1 * | 3/2001 | Boveja ........................ | 607/45 |
| 6,208,902 B1 * | 3/2001 | Boveja ........................ | 607/46 |
| 6,366,814 B1 * | 4/2002 | Boveja et al. ................ | 607/45 |
| 6,564,102 B1 * | 5/2003 | Boveja ........................ | 607/45 |

\* cited by examiner

*Primary Examiner*—Jeffrey R. Jastrzab

(57) ABSTRACT

An external pulse generator comprising a primary coil and adapted to inductively couple to an implanted receiving means, is designed to deliver neuromodulation therapy for disorders comprising obesity, eating disorders, anxiety and the like. The external pulse generator contains limited number of predetermined programs. These programs provide the patient or caretaker a means to adjust the therapy within confined limits, or turn the device off. The predetermined programs contain unique combination of pulse amplitude, pulse width, frequency of stimulation, and on-off time. In another mode of operation, the parameters can be individually adjusted and the stimulation therapy program can be "customized" for the patient, and stored in the memory. The programs are capable of being modified with a programming station connected to the pulse generator with a RS232-C serial connection. Additionally, the external pulse generator has two-way wireless capabilities, whereby enabling the physicians to remotely control the therapy programs of their patients using wireless internet. Moreover, the external pulse generator has proximity sensing and feedback regulation component to provide a constant therapy in accordance with the predetermined programs.

33 Claims, 25 Drawing Sheets

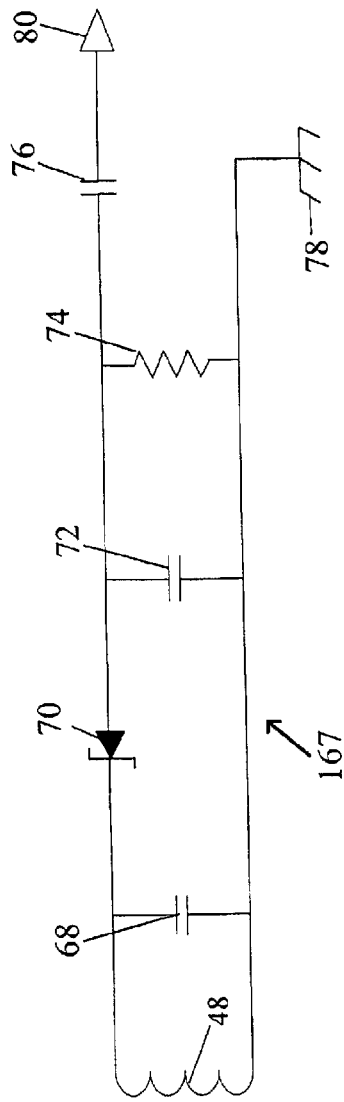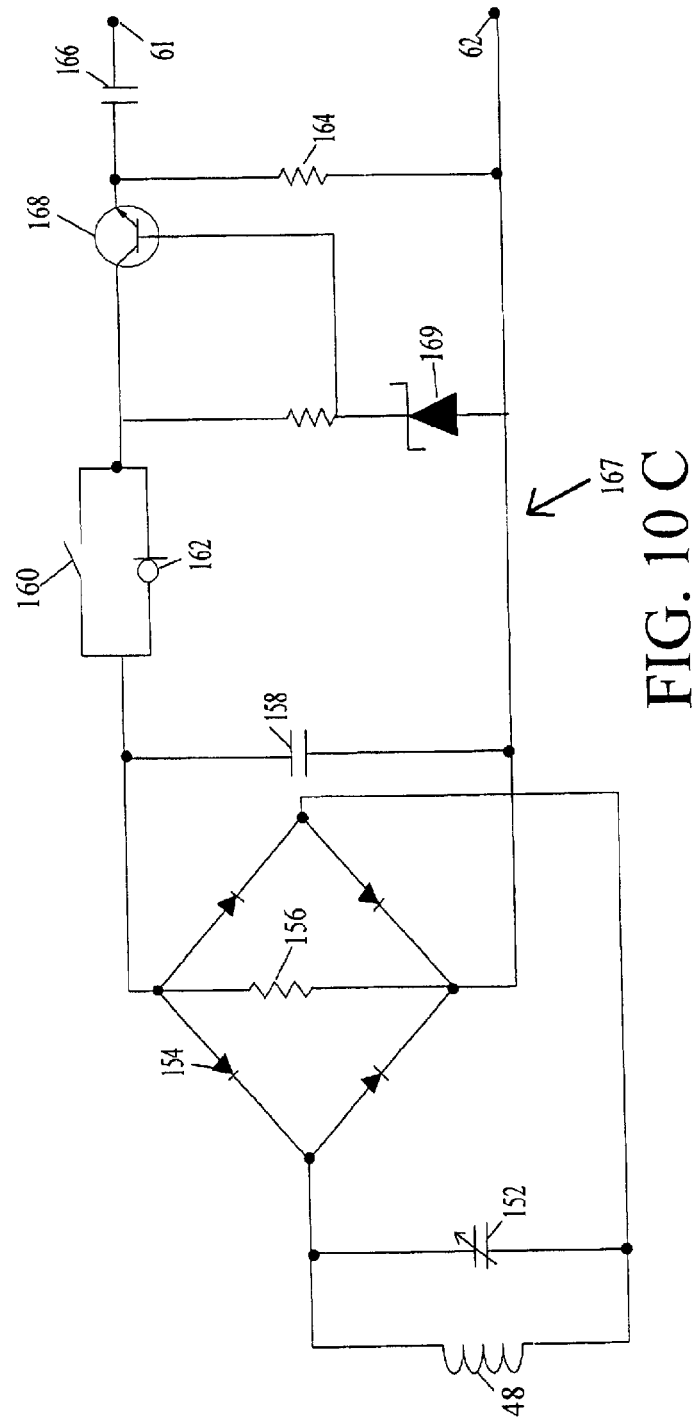
FIG. 10 B
FIG. 10 C

EXTERNAL PULSE GENERATOR FOR ADJUNCT (ADD-ON) TREATMENT OF OBESITY, EATING DISORDERS, NEUROLOGICAL, NEUROPSYCHIATRIC, AND UROLOGICAL DISORDERS

FIELD OF INVENTION

This is a Continuation-in-Part application of Ser. No. 09/751,966 filed Dec. 29, 2000, now U.S. Pat. No. 6,366,814 which is a Continuation-in-Part application of Ser. No. 09/178,060 filed Oct. 26, 1998, now U.S. Pat. No. 6,205,359. The prior applications being incorporated herein by reference.

This invention relates generally to electrical stimulation therapy for medical disorders, more specifically to neuromodulation therapy for obesity, eating disorders, and anxiety disorders with an external pulse generator (stimulator) containing predetermined programs, and adapted to be used with an implanted lead-receiver.

BACKGROUND

Obesity results from excessive accumulation of fat in the body. It is caused by ingestion of greater amounts of food than can be used by the body for energy. The excess food, whether fats, carbohydrates, or proteins, is then stored almost entirely as fat in the adipose tissue, to be used later for energy. There can be various causes of obesity including, psychogenic, neurogenic, genetic, and other metabolic related factors. Treatment of obesity depends on decreasing energy input below energy expenditure. Treatment has included among other things various drugs, starvation and even stapling or surgical resection of a portion of the stomach.

The vagus nerve (which is the $10^{th}$ cranial nerve) plays a role in mediating afferent information from the stomach to the satiety center in the brain. The vagus nerve arises directly from the brain, but unlike the other cranial nerves extends well beyond the head. At its farthest extension it reaches the lower parts of the intestines. This is shown schematically in FIG. 1A, and in more detail in FIG. 1B.

Observations on the profound effect of electrical stimulation of the vagus nerve on central nervous system (CNS) activity extends back to the 1930's. In 1988 it was reported in the *American Journal of Physiology*, that the afferent vagal fibers from the stomach wall increased their firing rate when the stomach was filled. One way to look at this regulatory process is to imagine that the drive to eat, which may vary rather slowly with the rise and fall of hormone Leptin, is inhibited by satiety signals that occur when we eat and begin the digestive process (i.e., the prandial period). As shown schematically in FIG. 1C, these satiety signals both terminate the meal and inhibit feeding for some time afterward. During this postabsorptive (fasting) period, the satiety signals slowly dissipate until the drive to eat again takes over.

The regulation of feeding behavior involves the concentrated action of several satiety signals such as gastric distention, the release of the gastrointestinal peptide cholecystokinin (CCK), and the release of the pancreatic hormone insulin. The stomach wall is richly innervated by mechanosensory axons, and most of these ascend to the brain via the vagus nerve. The vagus sensory axons activate neurons in the Nucleus of the Solitary Tract in the medulla of the brain. These signals inhibit feeding behavior. In a related mechanism, the peptide CCK is released in response to stimulation of the intestines by certain types of food, especially fatty ones. CCK reduces frequency of eating and size of meals. As shown schematically in FIG. 1D, both gastric distension and CCK act synergistically to inhibit feeding behavior.

Accordingly, appropriate extra-physiologic electrical stimulation of the vagus nerve, from just above the stomach level, should produce appetite supression by causing the patient to experience satiety. This is shown schematically in FIG. 1E. Alternatively, as shown in FIG. 1F, the vagus nerve may be stimulated at the level of the neck. Thereby, one aspect of the invention is directed to apparatus and method for electrical stimulation neuromodulation of the vagus nerve, to treat compulsive obesity and overeating with an implanted lead-receiver and an external stimulator. Upon experiencing the compulsive craving, the obese patient can voluntarily activate the stimulus generator by activating a predetermined program.

Medical research has also shown beneficial medical effects of vagus nerve stimulation (VNS) for anxiety disorders and other neurological disorders. Studies in clinical neurobiology have advanced our understanding of anatomic and physiologic basis of the anti-depressive effects of vagus nerve stimulation. As shown in FIG. 1G, cranial nerves have both afferent pathway 19 (inward conducting nerve fibers which convey impulses toward the brain) and efferent pathway 21 (outward conducting nerve fibers which convey impulses to an effector). The vagus nerve is composed of 80% afferent sensory fibers carrying information to the brain from the head, neck, thorax, and abdomen. The sensory afferent cell bodies of the vagus reside in the nodose ganglion and relay information to the nucleus tractus solitarius (NTS) 14. The vagus nerve is a direct extension of the brain; FIG. 1H, shows a diagram of the brain and spinal cord 24, with its relationship to the vagus nerve 54 and the nucleus tractus solitarius 14. FIG. 1I shows the relationship of the vagus nerve 54 with the other cranial nerves.

The vagus nerve relays information to nucleus of solitary tract and as shown schematically in FIG. 2, the nucleus of the solitary tract relays this incoming sensory information to the rest of the brain through three main pathways. These are, 1) an autonomic feedback loop, 2) direct projection to the reticular formation in the medulla, and 3) ascending projections to the forebrain largely through the parabrachial nucleus (PBN) 20 and the locus ceruleus (LC) 22. The PBN 20 sits adjacent to the nucleus LC 22 (FIG. 1H). The PBN/LC 20/22 sends direct connections to every level of the forebrain, including the hypothalamus 26, and several thalamic 25 regions that control the insula and orbitofrontal 28 and prefrontal cortices. Perhaps important for mood regulation, the PBN/LC 20/22 has direct connections to the amygdala 29 and the bed nucleus of the stria terminalis—structures that are implicated in emotion recognition and mood regulation.

In sum, incoming sensory (afferent) connections of the vagus nerve 54 provide direct projections to many of the brain regions implicated in nueropsychiatric disorders. These connections reveal how vagus nerve stimulation is a portal to the brainstem and connected regions. These circuits likely account for the neuropsychiatric effects of vagus nerve stimulation.

Increased activity of the vagus nerve is also associated with the release of more serotonin in the brain. Much of the pharmacologic therapy for treatment of migraines is aimed at increasing the levels of serotonin in the brain. Therefore, non-pharmacologic therapy of electrically stimulating the vagus nerve would have benefits for adjunct treatment of migraines and other ailments, such as obsessive compulsive disorders, that would benefit from increasing the level of serotonin in the brain.

The vagus nerve provides an easily accessible, peripheral route to modulate central nervous system (CNS) function. Other cranial nerves can be used for the same purpose, but the vagus nerve is preferred because of its easy accessibility. In the human body there are two vagal nerves (VN), the right VN and the left VN. Each vagus nerve is encased in the carotid sheath along with the carotid artery and jugular vein. The innervation of the right and left vagal nerves is different. The innervation of the right vagus nerve is such that stimulating it results in profound bradycardia (slowing of the heart rate). The left vagal nerve has some innervation to the heart, but mostly innervates the visceral organs such as the gastrointestinal tract. It is known that stimulation of the left vagal nerve does not cause any significant deleterious side effects.

Complex partial seizure is a common form of epilepsy, and some 30–40% of patients afflicted with this disorder are not well controlled by medications. Some patients have epileptogenic foci that may be identified and resected; however, many patients remain who have medically resistant seizures not amenable to resective surgery. Stimulation of the vagus nerve has been shown to reduce or abort seizures in experimental models. Early clinical trials have suggested that vagus nerve stimulation has beneficial effects for complex partial seizures and generalized epilepsy in humans. In addition, intermittent vagal stimulation has been relatively safe and well tolerated during the follow-up period available in these groups of patients. The minimal side effects of tingling sensations and brief voice abnormalities have not been distressing.

Most nerves in the human body are composed of thousands of fibers, of different sizes designated by groups A, B and C, which carry signals to and from the brain. The vagus nerve, for example, may have approximately 100,000 fibers of the three different types, each carrying signals. Each axon (fiber) of that nerve conducts only in one direction, in normal circumstances. The A and B fibers are myelinated (i.e., have a myelin sheath, constituting a substance largely composed of fat), whereas the C fibers are unmyelinated.

A commonly used nomenclature for peripheral nerve fibers, using Roman and Greek letters, is given in the table below,

| Group | External Diameter ($\mu$m) | Conduction Velocity (m/sec) |
| --- | --- | --- |
| Myelinated Fibers | | |
| A$\alpha$ or IA | 12–20 | 70–120 |
| A$\beta$: IB | 10–15 | 60–80 |
| II | 5–15 | 30–80 |
| A$\gamma$ | 3–8 | 15–40 |
| A$\delta$ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds ($\mu$s), for example. The A fiber conducts slightly faster than the B fiber and has a slightly lower threshold. The C fibers are very small, conduct electrical signals very slowly, and have high stimulation thresholds typically requiring a wider pulse width (300–1,000 $\mu$s) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents (i.e., inward conducting nerve fibers which convey impulses toward the brain) and efferents (i.e., outward conducting nerve fibers which convey impulses to an effector). Usually, nerve stimulation activates signals in both directions (bi-directionally). It is possible, however, through the use of special electrodes and waveforms, to selectively stimulate a nerve in one direction only (unidirectionally). The vast majority of vagal nerve fibers are C fibers, and a majority are visceral afferents having cell bodies lying in masses or ganglia in the skull. The central projections terminate largely in the nucleus of the solitary tract which sends fibers to various regions of the brain (e.g., the hypothalamus, thalamus, and amygdala).

The basic premise of vagal nerve stimulation for control of seizures is that vagal visceral afferents have a diffuse central nervous system (CNS) projection, and activation of these pathways has a widespread effect on neuronal excitability.

The cervical component of the vagus nerve (10th cranial nerve) transmits primarily sensory information that is important in the regulation of autonomic activity by the parasympathetic system. General visceral afferents constitute approximately 80% of the fibers of the nerve, and thus it is not surprising that vagal nerve stimulation (VNS) can profoundly affect CNS activity. With cell bodies in the nodose ganglion, these afferents originate from receptors in the heart, aorta, lungs, and gastrointestinal system and project primarily to the nucleus of the solitary tract which extends throughout the length of the medulla oblongata. A small number of fibers pass directly to the spinal trigeminal nucleus and the reticular formation.

As might be predicted from the electrophysiologic studies, the nucleus of the solitary tract has widespread projection to cerebral cortex, basal forebrain, thalamus, hypothalamus, amygdala, hippocampus, dorsal raphe, and cerebellum as shown in FIG. 2 (from Epilepsia, vol. 3, suppl. 2: 1990, page S2).

In the mid-1980s it was suggested that electrical stimulation of the vagus nerve might be effective in preventing seizures. Early studies on the effects of vagal nerve stimulation (VNS) on brain function focused on acute changes in the cortical electroencephalogram (EEG) of anesthetized animals. Investigators found that VNS could temporarily synchronize or desynchronize the electroencephalogram, depending on the level of anesthesia and the frequency or intensity of the vagal stimulus. These observations had suggested that VNS exerted its anticonvulsant effect by desynchronizing cortical electrical activity. However, subsequent clinical investigations have not shown VNS-induced changes in the background EEGs of humans. A study, which used awake and freely moving animals, also showed no VNS-induced changes in background EEG activity. Taken together, the findings from animal study and recent human studies indicate that acute desynchronization of EEG activity is not a prominent feature of VNS when it is administered during physiologic wakefulness and sleep, and does not explain the anticonvulsant effect of VNS.

The mechanism by which vagal nerve stimulation (VNS) exerts its influence on seizures is not entirely understood. An early hypotheses had suggested that VNS utilizes the relatively specific projection from the nucleus of the solitary track to limbic structures to inhibit partial seizures, particularly those involving cortex, which regulates autonomic activity or visceral sensations such as in temporal lobe epilepsy. Afferent VNS at the onset of a partial seizure could abort the seizure in the same way somatosensory stimuli can abort a seizure from the rolandic cortex; however, chronic intermittent stimulation may also produce an alteration in limbic circuitry that outlasts the stimulus and decreases epileptogenesis or limits seizure spread. Support for this hypothesis comes from studies of fos immunoreactivity in the brain of rats in response to VNS. Fos is a nuclear protein resulting from expression of early immediate genes in highly active neurons. VNS causes a specific fos immunolabeling in amygdala and limbic neocortex, suggesting that the antiepileptic effect may be mediated in these areas. Such activation of genetic mechanisms could account for the apparent sustained antiepileptic effect of intermittent stimulation.

Another possible mechanism that is being explored to explain an antiseizure effect of VNS is activation of the brainstem noradrenergic nuclei, locus ceruleus and A5, which also show fos immunolabeling. Noradrenergic mechanisms are well known to influence seizure activity in genetic epilepsy-prone rats, and the anticonvulsant effects of VNS against maximal electroshock seizures can be blocked inactivation of the locus ceruleus. Woodbury and Woodbury (1990) suggested that VS acts through increasing release of glycine or GABA since seizures induced by both PTZ and strychnine can be blocked by VNS. Other neurotransmitter systems may also be implicated since VNS increases cerebrospinal fluid homovanilic acid and 5-hydroxyindoleacetate, suggesting modulation of dopaminergic and serotonergic systems. Finally, a nonspecific alteration of activity in the brainstem reticular system with subsequent arousal must be considered.

VNS appears to have similar efficacy in both partial and generalized seizures in experimental models and in human epilepsy consistent with a nonspecific effect. Furthermore, the same inhibition of interictal corticalspike activity as seen with VNS occurs in animals during electrical stimulation of the midbrain reticular formation or with thermal stimulation of somatosensory nerves in the rat tail. Reduction of experimental generalized spike wave by arousal has also been documented. Similarly, nonspecific afferent stimulation has been well demonstrated in humans to suppress focal spikes, generalized spike waves, and seizures.

VNS may inhibit seizures directly at the level of cerebral cortical neuronal irritability, or at the level of diffuse ascending subcortical projection systems, or both. Thus, VNS is also well suited for the treatment of medication-resistant symptomatic generalized epilepsy (SGE), in which, characteristically both focal and generalized features are found on interictal EEGs and also in clinical seizure types.

Now considering the background of urinary urge incontinence. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder and urethra are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor 192 (muscle in the wall of the urinary bladder) contraction, as depicted schematically in FIG. 3. These receptors have high dynamic sensitivity and are easily activated by external pressure transients, as may occur during coughing or tapping of the abdominal wall. Their faithful response to active changes in bladder pressure is well illustrated.

When sufficiently activated, the mechanorecptors trigger a coordinated micturition reflex via a center in the upper pons 187, (FIG. 3). The reflex detrusor 192 contraction generates an increased bladder pressure and an even stronger activation of the mechanoreceptors. Their activity in turn reinforces the pelvic motor output to the bladder, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 190, which increases its activity in response to bladder mechanoreceptor activation during filling. An analogous mechanism is Edvardsen's reflex, which involves mechanoreceptor activation of inhibitory sympathetic neurons to the bladder. The sympathetic efferents have a dual inhibitory effect, acting both at the post-ganglionic neurons in the vesical ganglia and directly on the detrusor muscle 192 of the bladder. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneously. The symptomatic pattern also usually is consistent over long periods.

Based on clinical experience, subtypes of urge incontinence include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency. Electrostimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that uses electrical stimulation of the sacral nerves, (a general diagram of spinal cord and sacral nerves 185 is shown in FIG. 4). The aim of this treatment modality is to achieve detrusor 192 inhibition by chronic electrical stimulation of afferent somatic sacral nerve fibers 185 via implanted electrodes coupled to a subcutaneously placed pulse generation means.

The rationale of this treatment modality is based on the existence of spinal inhibitory systems that are capable of interrupting a detrusor 192 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 185. Of the sacral nerve roots the S3 root is the most practical for use in chronic electrical stimulation. In neuromodulation, the entire innervation system should be intact. As shown schematically in FIG. 5, the procedure consists of placing electrodes 61, 62 in one of the sacral foraman as close to the pelvic plexus and pudendal nerve as possible and connecting the lead 179 with a means for electrical stimulation 49. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus 25. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branches of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 185. Sacral nerve 185 stimulation is based on research dedicated to the understanding of the voiding reflex as well as the role and influence of the sacral nerves 185 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 185.

Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibition in this setting, though data supporting this hypotheses are lacking. In summary, the rationale for neuromodulation in the management of such patients is the observation that stimulation of the sacral nerves via electrical stimulation can inhibit inappropriate neural reflex behavior.

PRIOR ART

One type of prior art non-pharmacological therapy for obesity, eating disorders, and anxiety disorders is generally directed to the use of an implantable lead and an implantable pulse generator technology or "cardiac pacemaker-like" technology.

U.S. Pat. No. 5,263,480 (Wernicke et al) is generally directed to treatment of eating disorders by using an implantable neurocybernetic prosthesis (NCP), which is a "cardiac pacemaker-like" device.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet use and tapping sequence.

U.S. Pat. No. 3,796,221 (Hagfors) is directed to controlling the amplitude, duration and frequency of electrical stimulation applied from an externally located transmitter to an implanted receiver by inductive coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy needs to be continuously sustained over a prolonged period of time. The methodology disclosed is focused on circuitry within the receiver, which would not be sufficient when the transmitting coil and receiving coil assume significantly different orientation, which is likely in the current application.

U.S. Pat. Nos. 4,702,254, 4,867,164 and 5,025,807 (Zabara) generally disclose animal research and experimentation related to epilepsy and the like and are directed to stimulating the vagus nerve by using "pacemaker-like" technology, such as an implantable pulse generator. The pacemaker technology concept consists of a stimulating lead connected to a pulse generator (containing the circuitry and DC power source) implanted subcutaneously or submuscularly, somewhere in the pectoral or axillary region, and programming with an external personal computer (PC) based programmer. Once the pulse generator is programmed for the patient, the fully functional circuitry and power source are fully implanted within the patient's body. In such a system, when the battery is depleted, a surgical procedure is required to disconnect and replace the entire pulse generator (circuitry and power source). These patents neither anticipate practical problems of an inductively coupled system, nor suggest solutions to the same for an inductively coupled system for neuromodulation therapy.

U.S. Pat. No. 4,573,481 (Bullara) is directed to an implantable helical electrode assembly configured to fit around a nerve. The individual flexible ribbon electrodes are each partially embedded in a portion of the peripheral surface of a helically formed dielectric support matrix.

U.S. Pat. No. 3,760,812 (Timm et al.) discloses nerve stimulation electrodes that include a pair of parallel spaced apart helically wound conductors maintained in this configuration.

An implantable pulse generator and lead with a PC based external programmer is specifically advantageous for cardiac pacing applications for several reasons, including:

1) A cardiac pacemaker must sense the intrinsic activity of the heart, because cardiac pacemakers deliver electrical output primarily during the brief periods when patients either have pauses in their intrinsic cardiac activity or during those periods of time when the heart rate drops (bradycardia) below a certain pre-programmed level. Therefore, for most of the time, in majority of patients, the cardiac pacemaker "sits" quietly monitoring the patient's intrinsic cardiac activity.

2) The stimulation pulse frequency for cardiac pacing is typically close to 1 Hz, as opposed to approximately 20 Hz or higher, typically used in nerve stimulation applications.

3) Patients who require cardiac pacemaker support are typically in their 60's, 70's or 80's years of age.

The combined effect of these three factors is that the battery in a pacemaker can have a life of 10–15 years. Most patients in whom a pacemaker is indicated are implanted only once, with perhaps one surgical pulse generator replacement.

In contrast, patients with neurological disorders in whom electrical stimulation is beneficial are much younger as a group. Also, stimulation frequency is typically 20 Hz or higher, and the total stimulation time per day is much longer than is typical for cardiac pacemakers. As a result, battery drain is typically much higher for nerve stimulation applications than for cardiac pacemakers.

The net result of these factors is that the battery will not last nearly as long as in cardiac pacemakers. Because the indicated patient population is also much younger, the expense and impact of surgical generator replacement will become significant, and detract from the appeal of this therapy. In fact, it has been reported in the medical literature that the battery life can be as short as one and half years for implantable nerve stimulator. (R. S McLachlan, p. 233).

There are other advantages of the present inductively coupled system.

1) The hardware components implanted in the body are much less. This is specifically advantageous for the patient in terms of patient comfort, and it decreases the chances of the hardware getting infected in the body. Typically, when an implantable system gets infected in the body, it cannot be easily treated with antibiotics and eventually the whole implanted system has to be explanted.

2) Because the power source is external, the physician can use stimulation sequences that are more effective and more demanding on the power supply, such as longer "on" time.

3) With the controlling circuitry being external, the physician and the patient may easily select from a number of predetermined programs, override a program, manually operate the device or even modify the predetermined programs.

4) The external pulse generator does not need to be monitored for "End-of-Life" (EOL) like the implantable system, thus resulting in cost saving and convenience.

5) The current system can be manufactured at a significantly lower cost of an implantable pulse generator and programmer system, providing the patient and medical establishment with cost effective therapies.

6) With a telemetry module embedded in the current system, remote wireless communication directly with the external stimulator is more practical.

SUMMARY OF THE INVENTION

The external pulse generator of the present invention, has a primary coil adapted to be coupled with a subcutaneous secondary coil of an implanted receiving means for neuromodulation treatment of obesity, compulsive eating disorders, and anxiety disorders. The adjunct (add-on) treatment of the specific therapy being used depends upon the specific predetermined program being used, along with the nerve bundle being stimulated. Each predetermined program consists of unique combination of pulse amplitude, pulse-width, frequency of stimulation, and on-off time periods.

In one aspect of the invention the pulse generator contains a limited number of predetermined programs, which can be accessed directly without a programmer. The limited number of programs can be any number of programs up to as many as 100 programs, and such a number is considered within the scope of this invention. For convenience and ease of use, the presently preferred embodiment contains less than 20 predetermined programs. There is an option to make at least one of these programs locked out to the patient or caretaker, and be accessible only by the medical personnel.

In another aspect of the invention, the patient can selectively activate any program within the confines of patient-available programs, or turn the device off.

In another aspect of the invention, the physician can select the value of each parameter individually from a range of values, and program the device to the unique combination of parameters for the patient.

In another aspect of the invention, the pre-determined programs can be modified with a programming station connected to the pulse generator with a RS232-C serial connection.

In another aspect of the invention, the pulse generator contains a module for remote wireless two-way communication. This module enables remotely, to control the neuromodulation therapy for obesity, compulsive eating disorders, and anxiety disorders.

In yet another aspect of the invention, the pulse generator contains circuitry for proximity sensing and feedback control.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

DESCRIPTION OF THE INVENTION

Figure 1A:
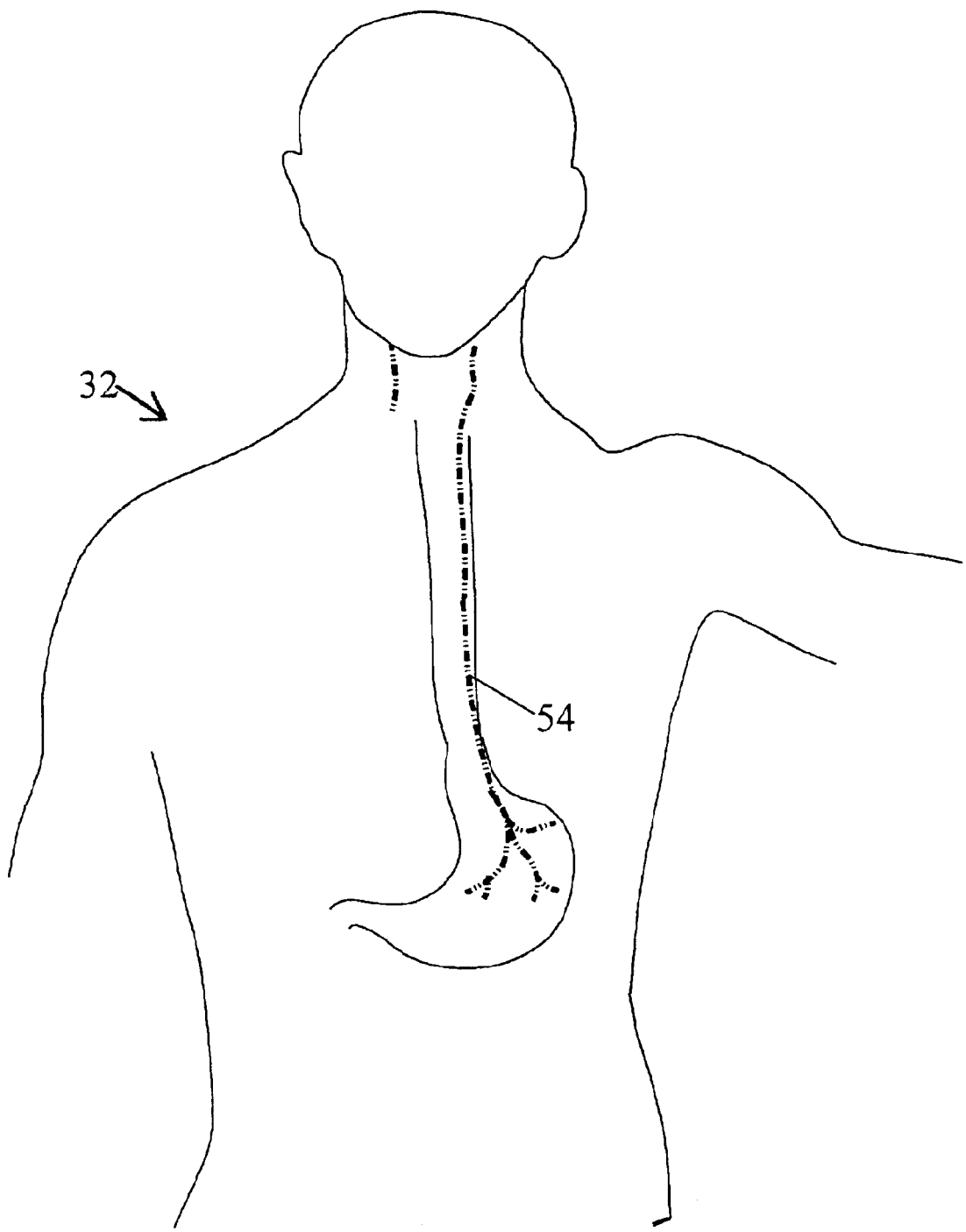
FIG. 1A is a schematic drawing showing innervation of the left vagus nerve to the stomach area.
Figure 1B:
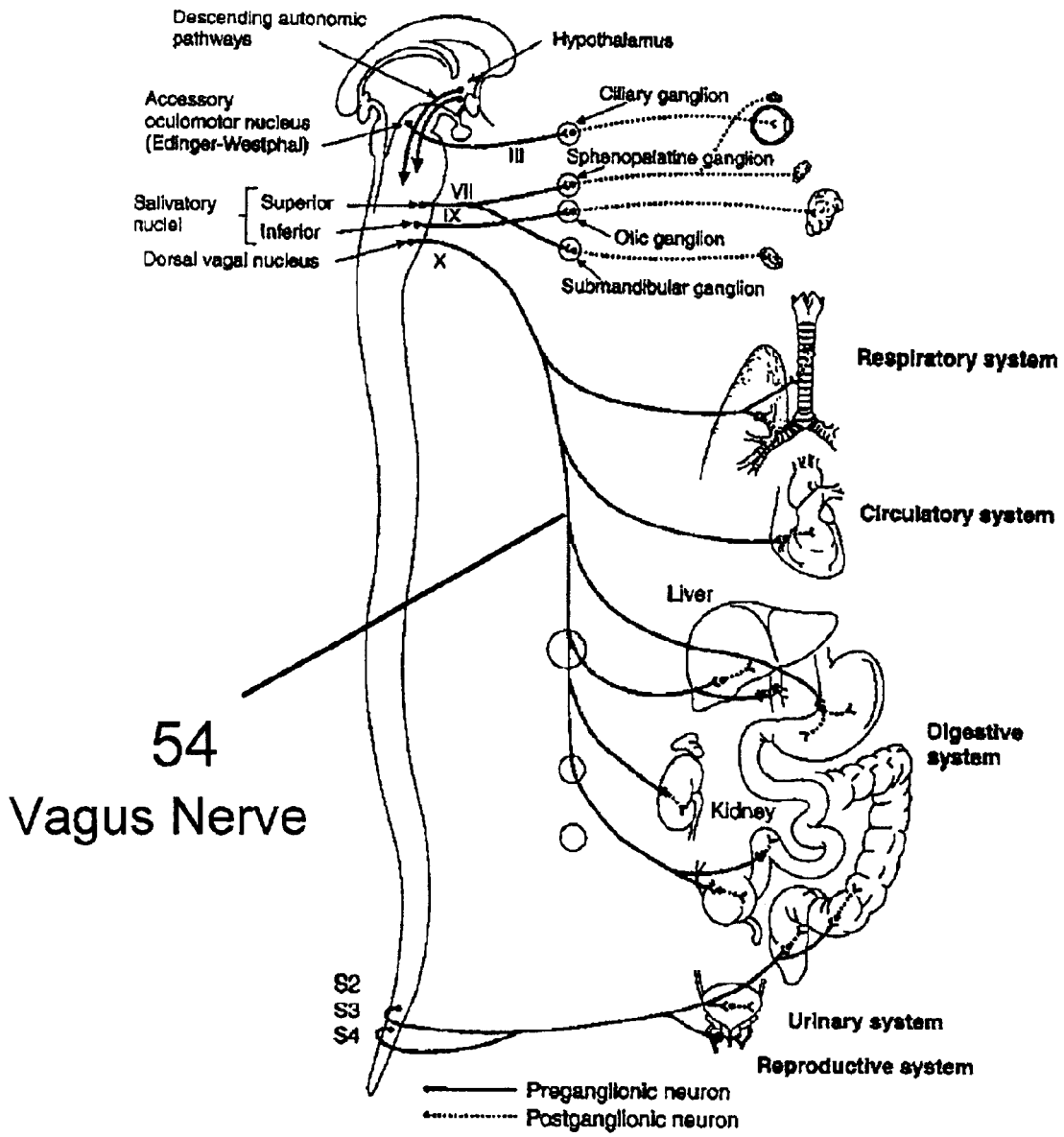
FIG. 1B is a schematic drawing showing detailed innervation of the left vagus nerve to the thoracic and viceral organs.
Figure 1C:
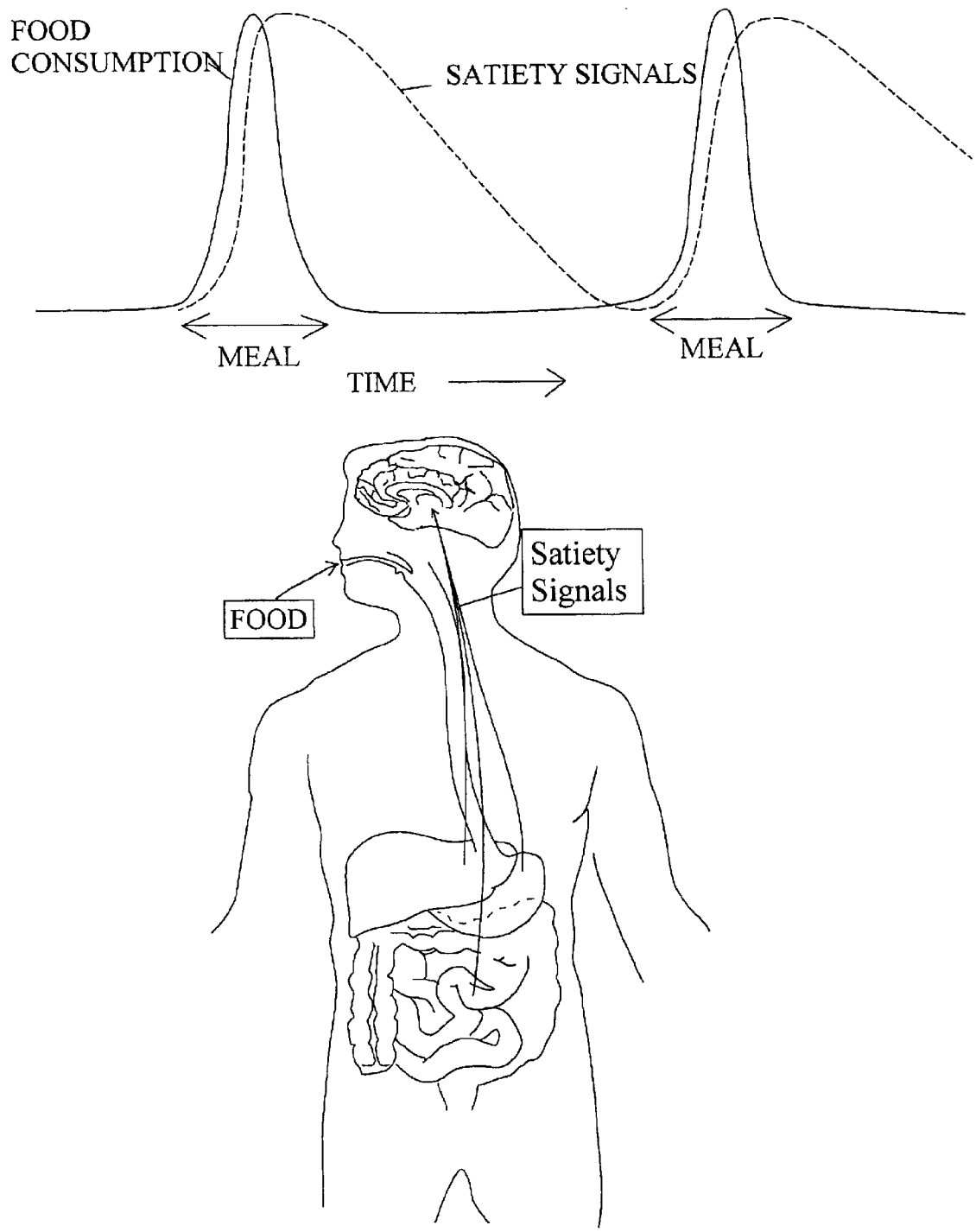
FIG. 1C is a schematic diagram showing the relationship of meals and satiety signals.
Figure 1D:
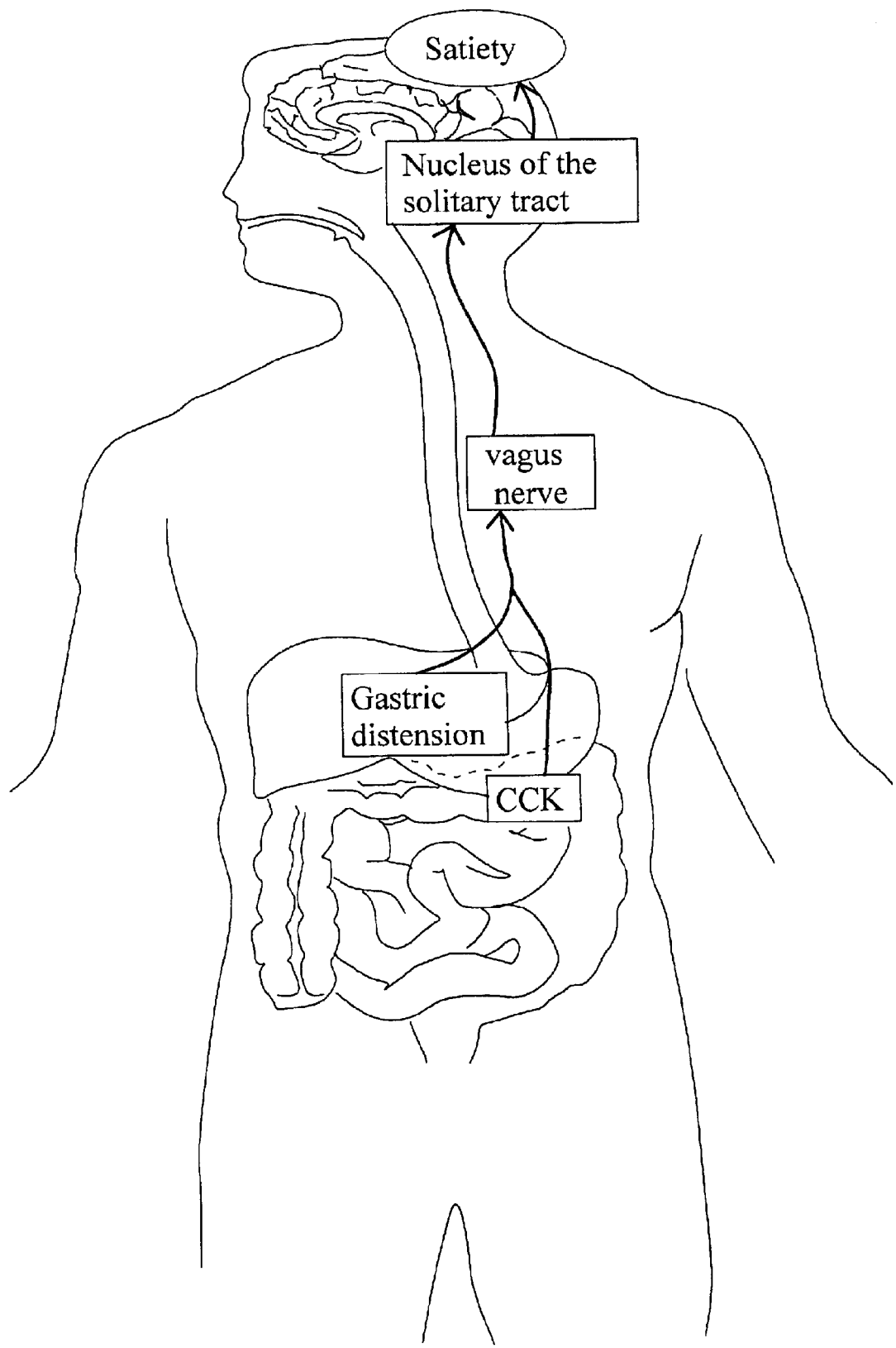
FIG. 1D is a schematic diagram showing impulses traveling via the vagus nerve in response to gastric distention and CCK release.
Figure 1F:
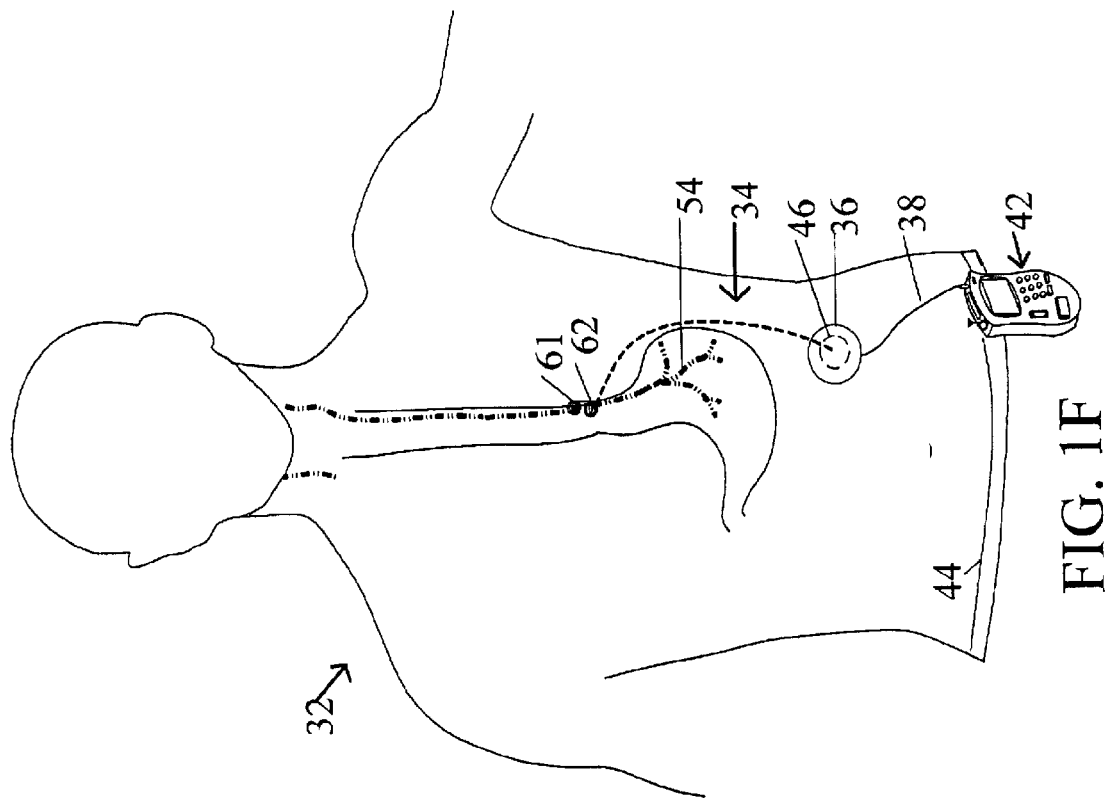
FIG. 1F is a schematic diagram of a patient with an implanted read receiver and an external stimulator showing vagal nerve stimulation at the neck level.
Figure 1E:
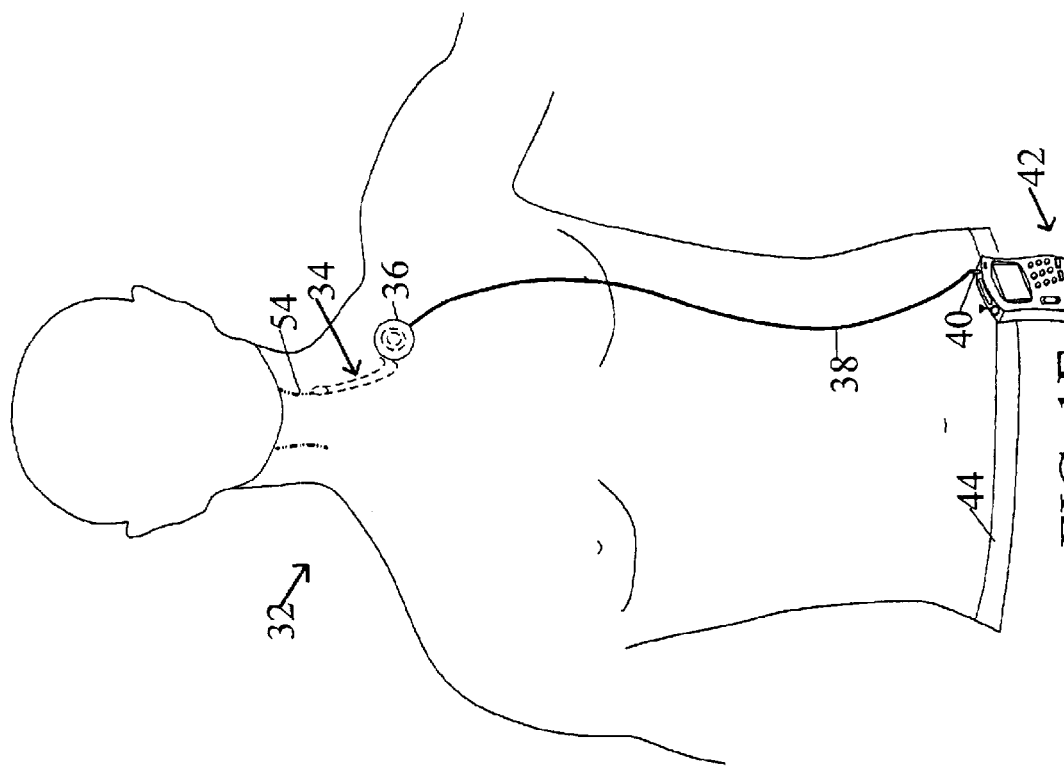
FIG. 1E is a schematic diagram of a patient with an implanted read receiver and an external stimulator showing vagal nerve stimulation at the stomach level.
Figure 1G:
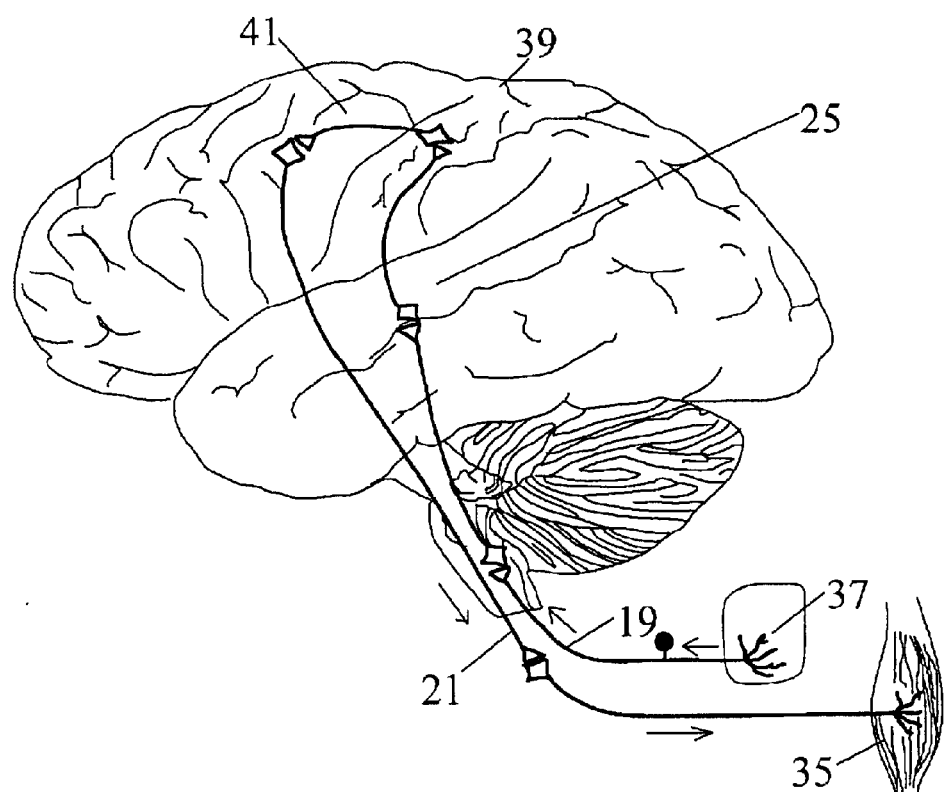
FIG. 1G is a diagram of brain showing afferent and efferent pathways.
Figure 1H:
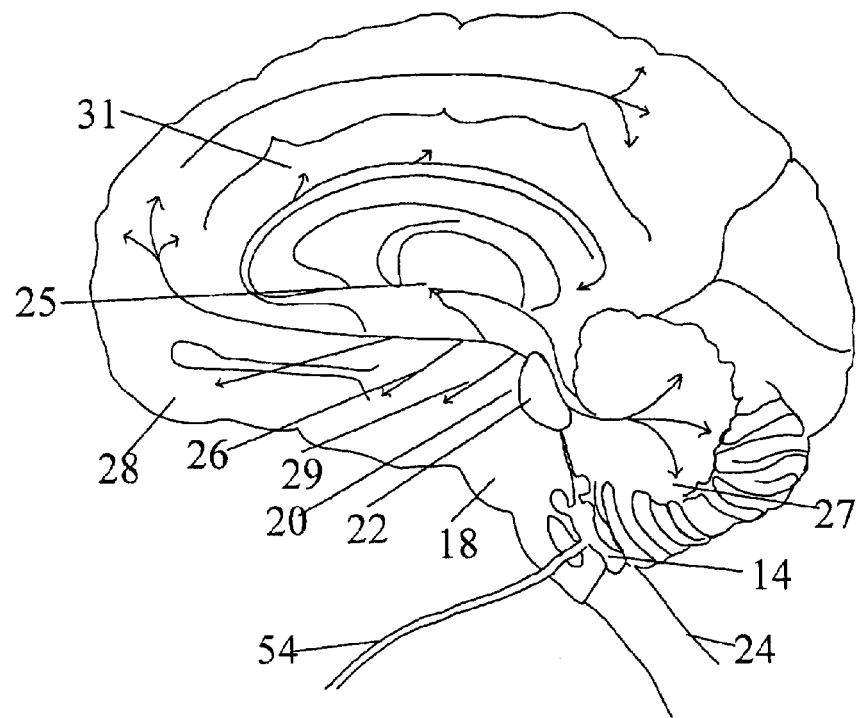
FIG. 1H is a diagram of the lateral view of brain and spinal cord, with its relationship to the vagus nerve.
Figure 1I:
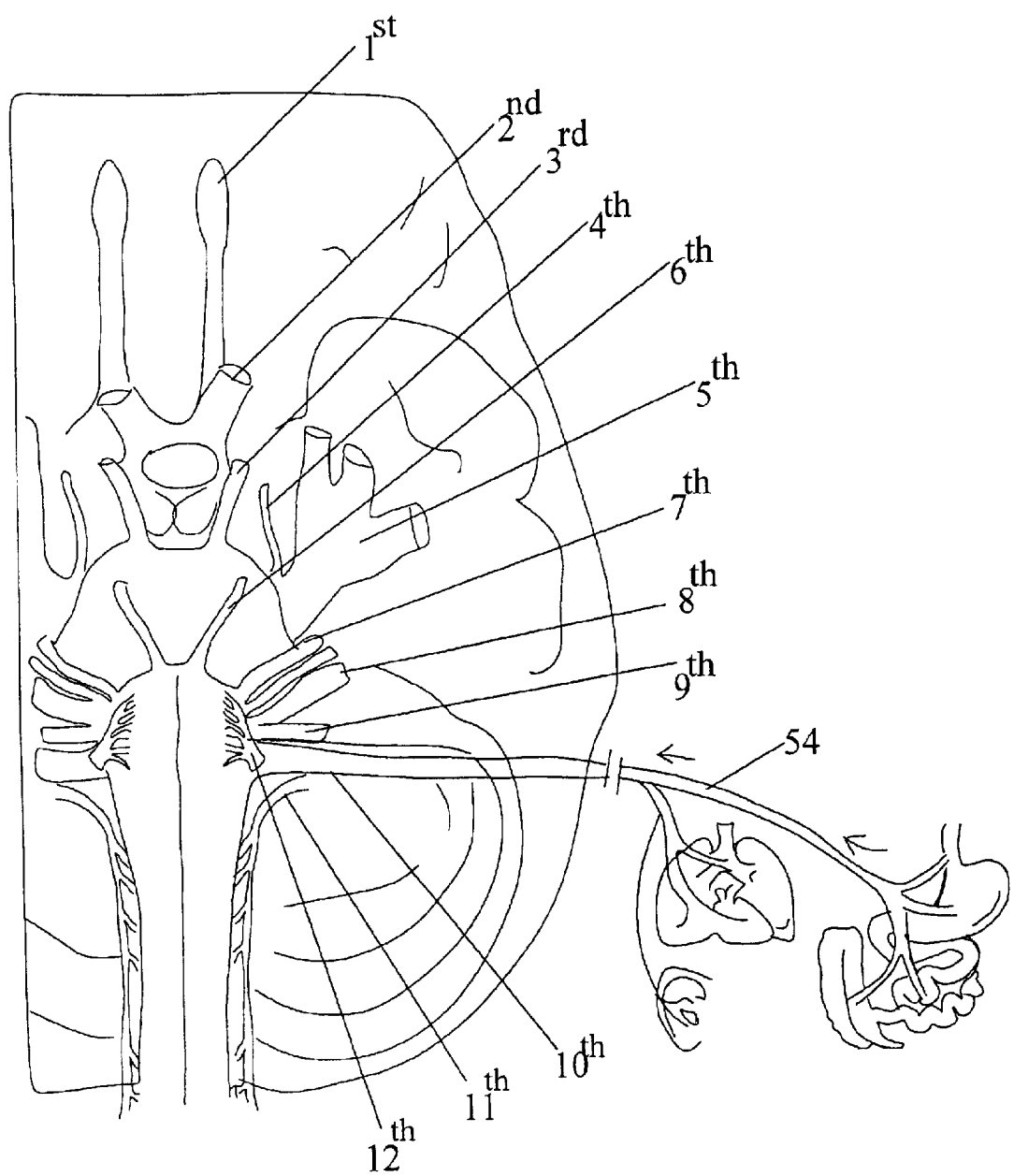
FIG. 1I is a schematic diagram of the base of brain showing the relationship of vagus nerve to the other cranial nerves.
Figure 2:
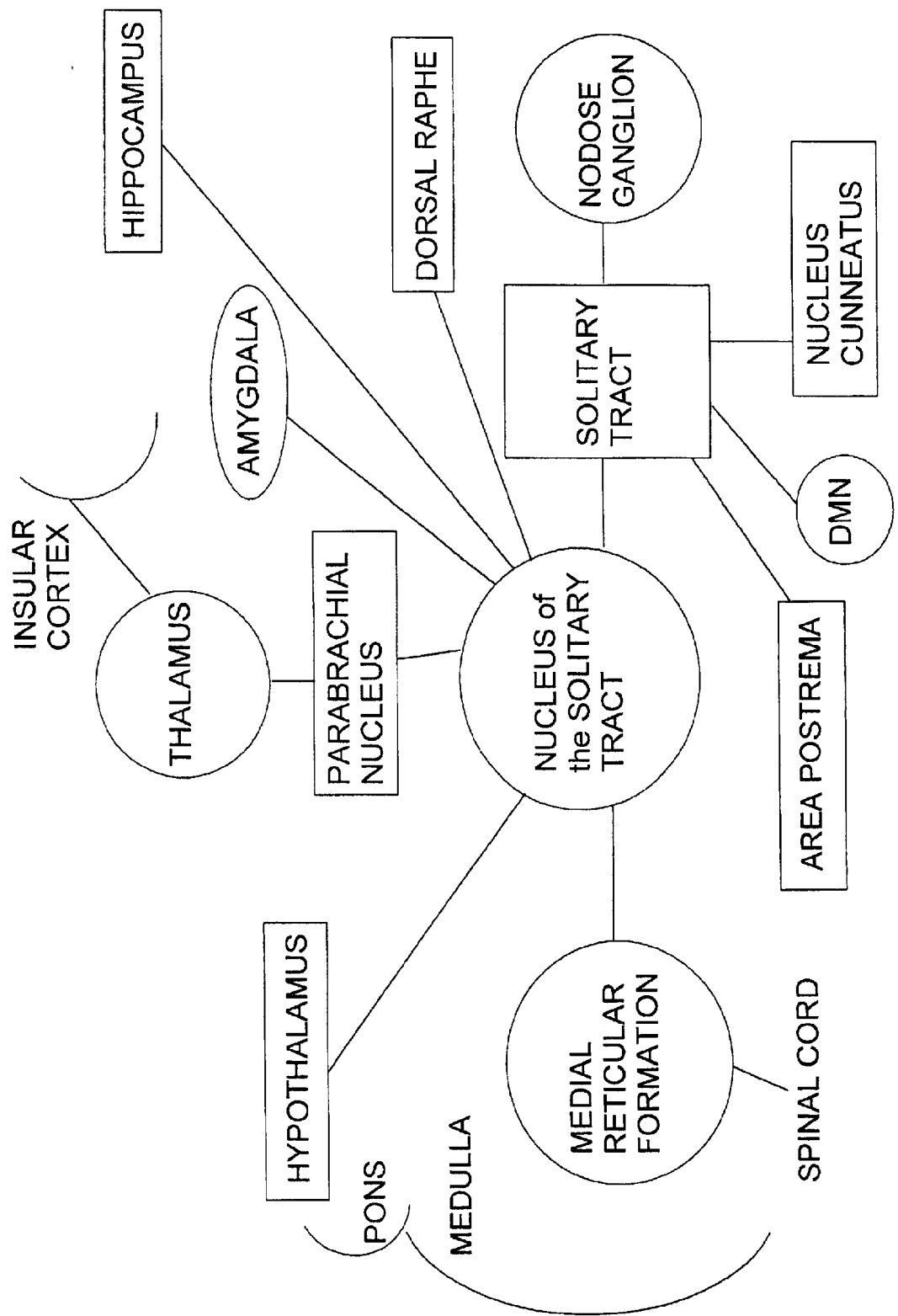
FIG. 2 is a schematic showing the relationship of nucleus of solitary tract with other structures of the brain.
Figure 3:
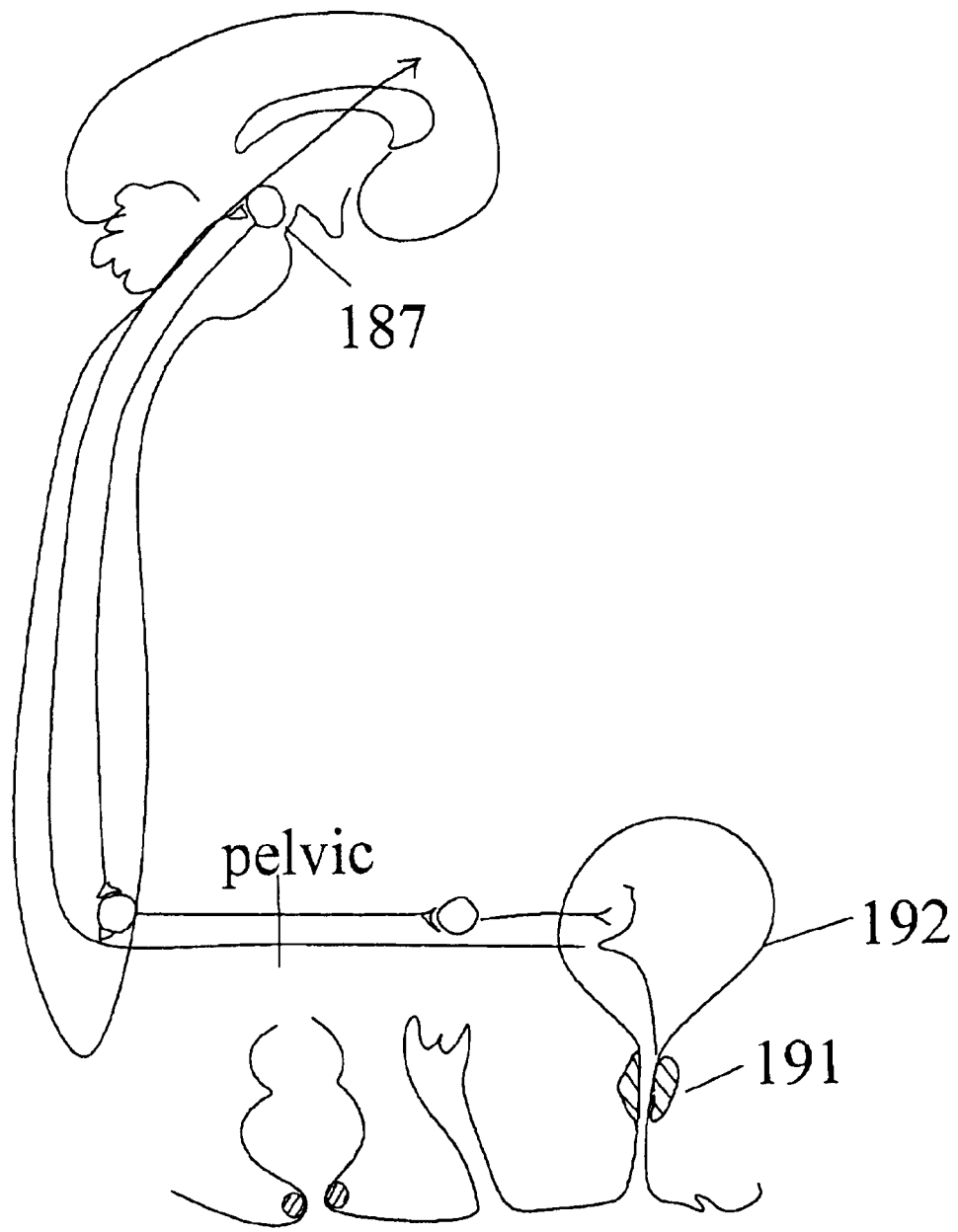
FIG. 3 is a schematic diagram showing physiological control of micturition.
Figure 4:
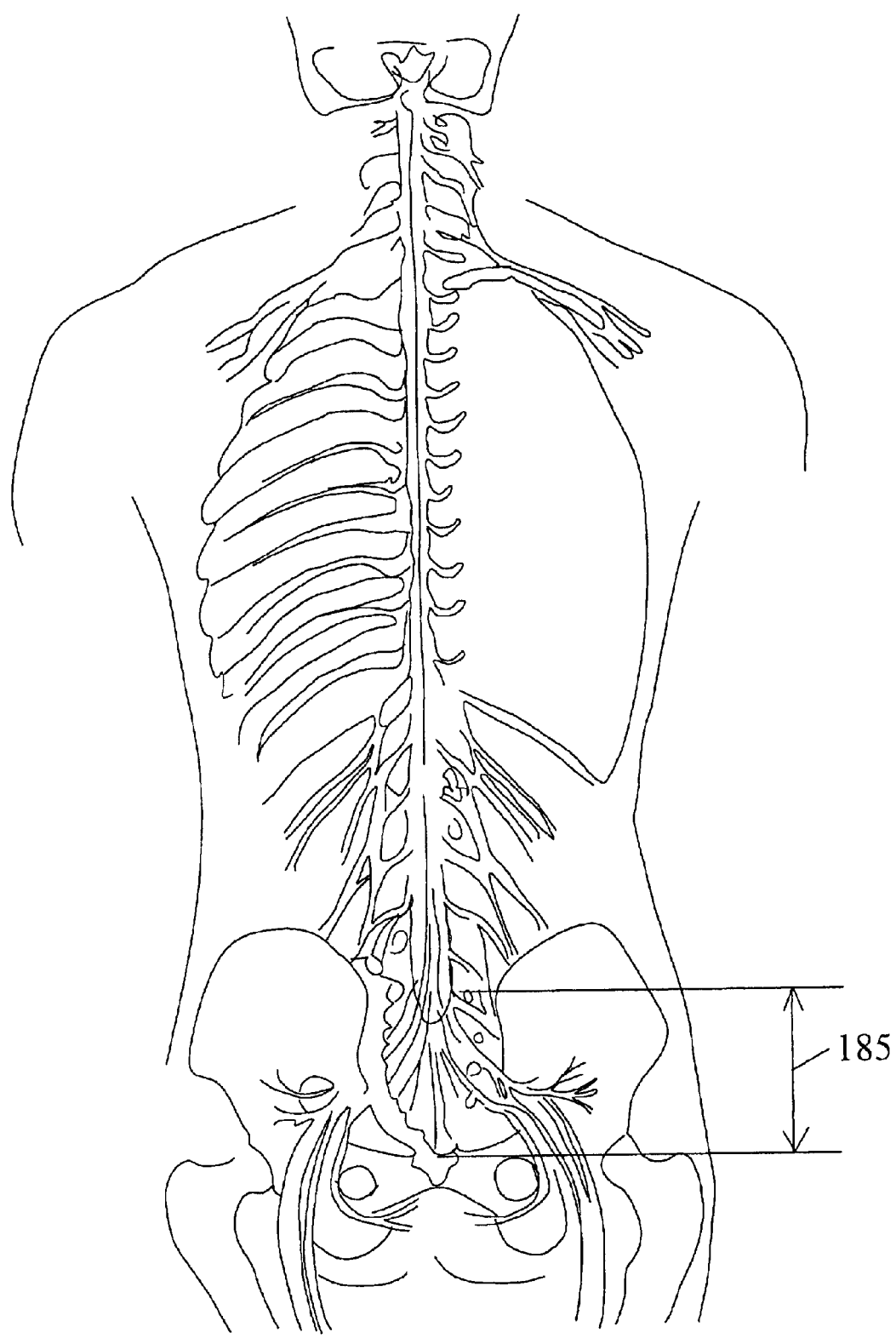
FIG. 4 is a diagram showing anatomic relationships of spinal nerves and sacral plexus.
Figure 5:
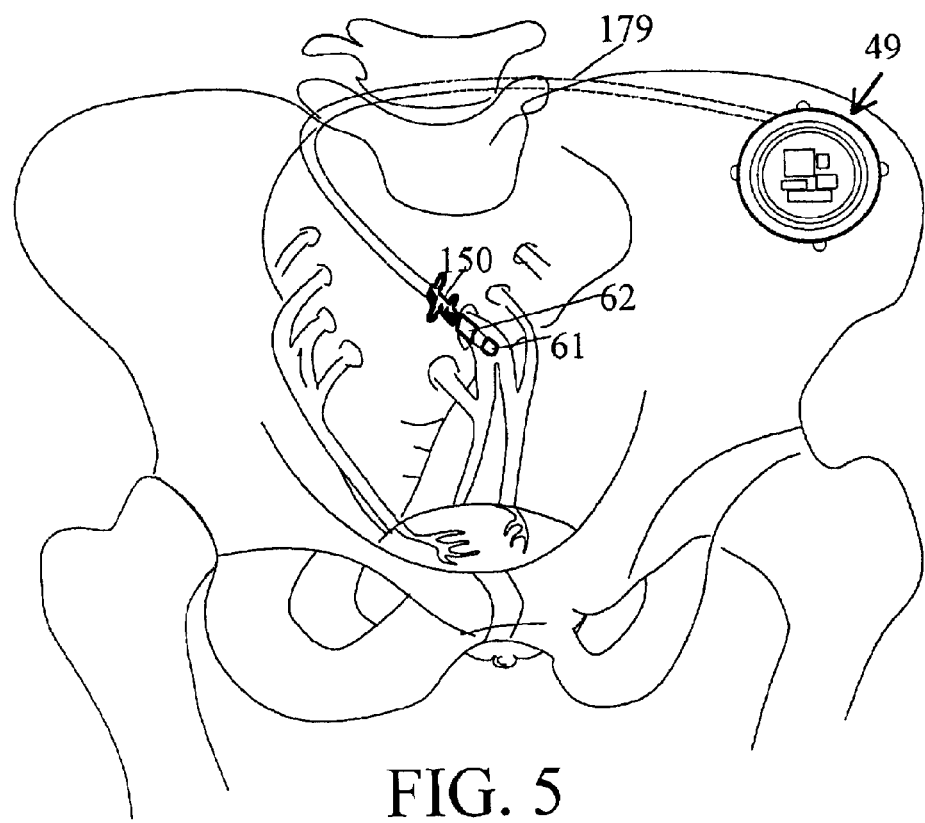
FIG. 5 is a schematic diagram of the sacral region showing electrodes in sacral foraman, and placement of the lead-receiver.

FIGS. 1E and 1F show schematic diagrams of a patient 32 with an implantable lead-receiver 34 and an external pulse generator (stimulator) 42, clipped on to a belt 44 in this case. The external stimulator 42 may alternatively be placed in a pocket or other carrying device. The external stimulator 42 is adapted to work with an implanted lead-receiver 34. The primary coil 46 of the external pulse generator 42 inductively transfers pulses to the implanted lead-receiver 34, which is also in electrical connection with the nerve tissue at the distal end.

Figure 6:
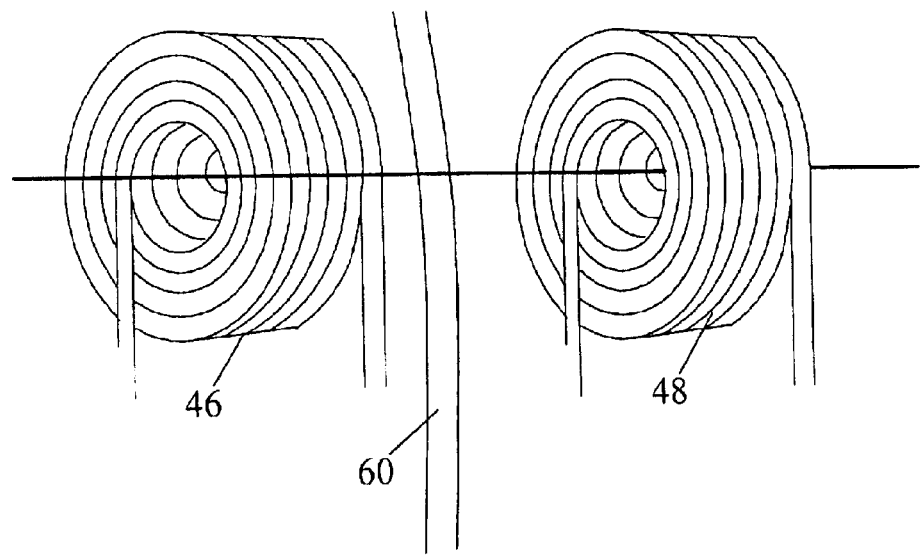
FIG. 6 is a diagram showing two coils along their axis, in a configuration such that the mutual inductance would be maximum.
Figure 7:
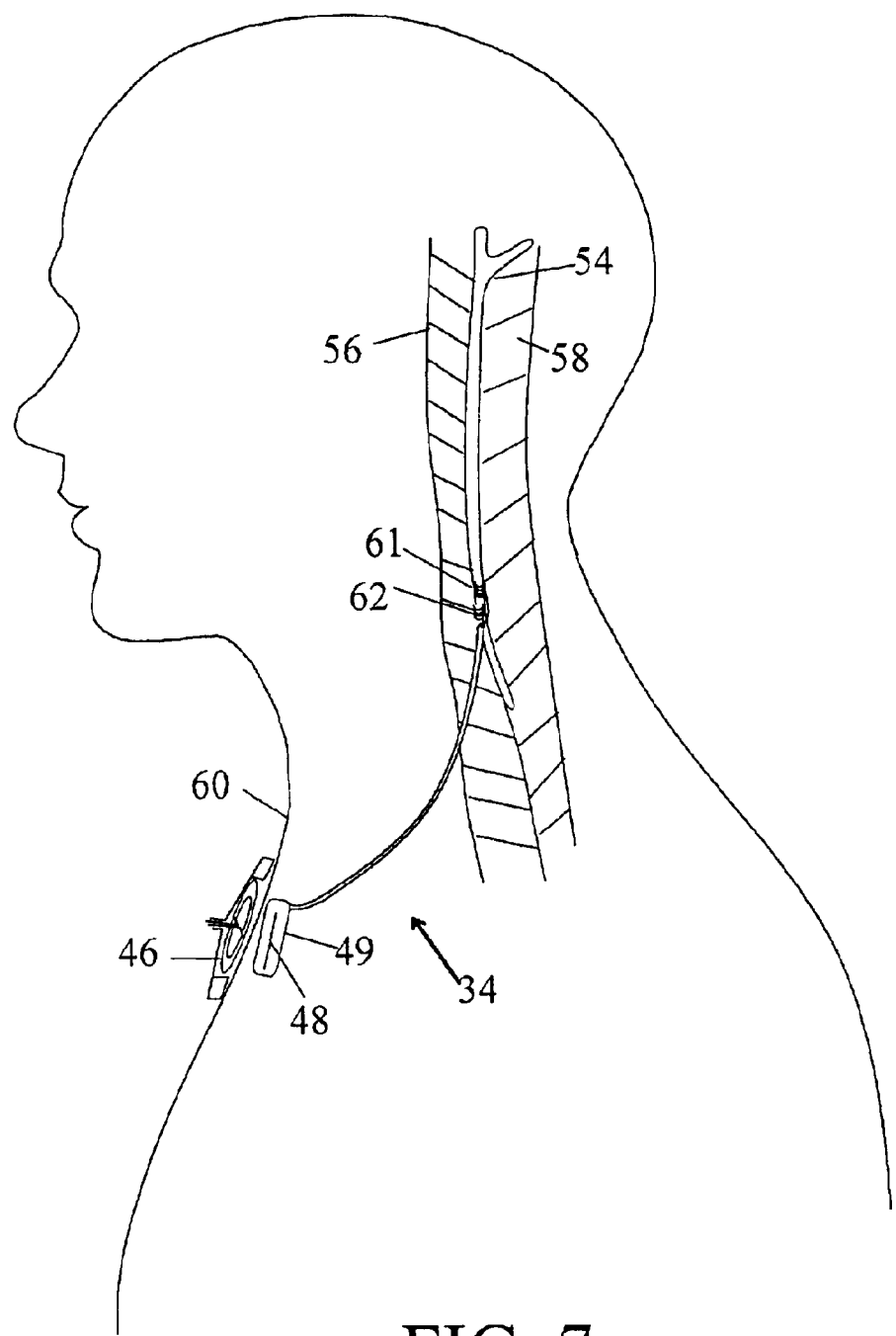
FIG. 7 is a diagram showing the effects of two coils with axes at right angles.

As shown in FIG. 6, when two coils are arranged with their axes on the same line, current sent through coil 46 creates a magnetic field that cuts coil 48 which is placed subcutaneously. Consequently, a voltage will be induced in coil 48 whenever the field strength of coil 46 is changing. This induced voltage is similar to the voltage of self-induction but since it appears in the second coil because of current flowing in the first, it is a mutual effect and results from the mutual inductance between the two coils. The degree of coupling of these two coils depends upon the physical spacing between the coils and how they are placed with respect to each other. Maximum coupling exists when they have a common axis and are as close together as possible (but separated by skin). The coupling is least when the coils are far apart or are placed so their axes are at right angles. As shown in FIG. 7, the secondary coil 48 inside the lead-receiver 34 is approximately along the same axis as the primary coil 46.

Figures 8, 9:
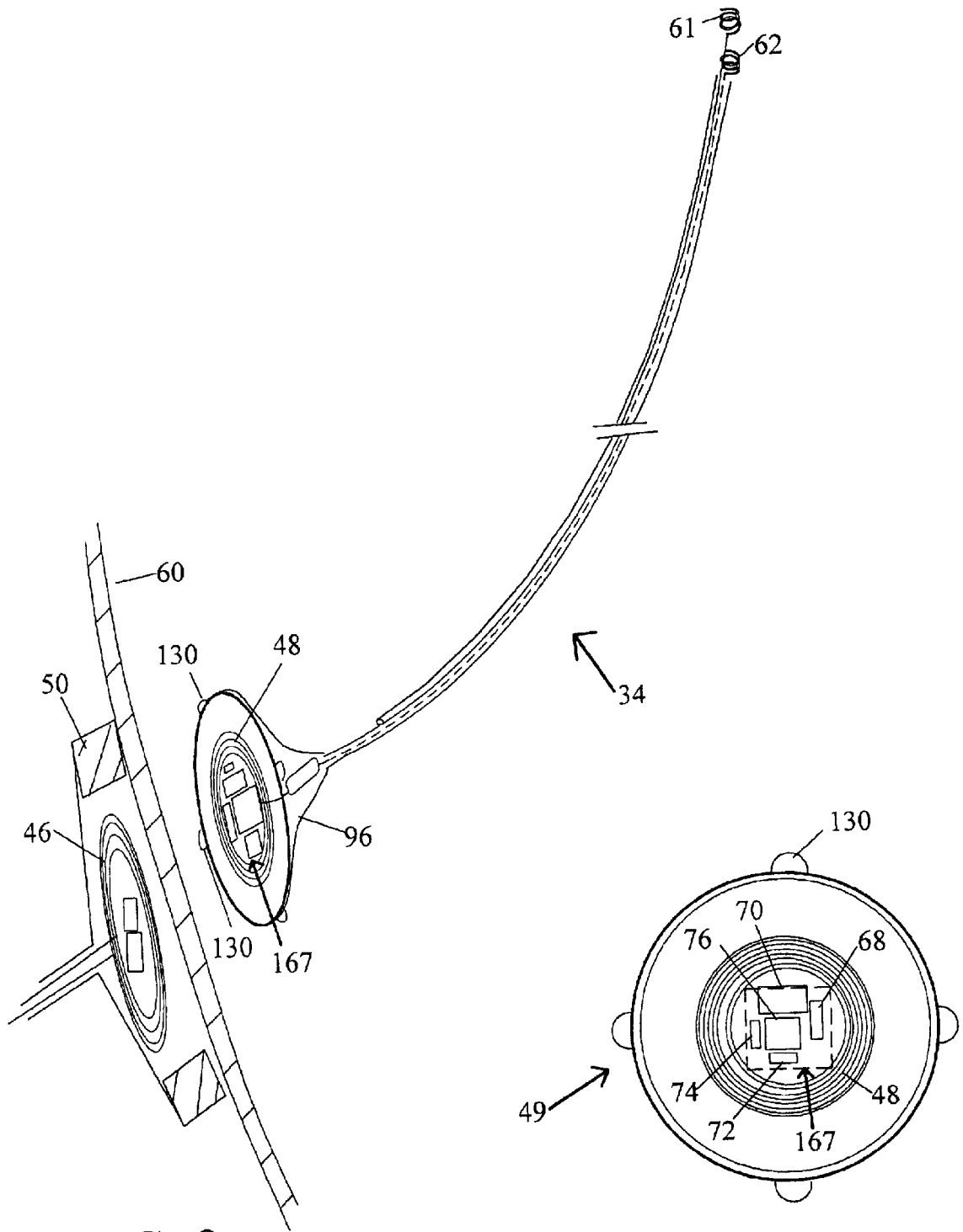
FIG. 8 is a diagram showing the implanted lead-receiver and the transmitting coil.
FIG. 9 is a diagram showing the proximal end of the lead-receiver.

FIG. 8 shows a schematic diagram of the implantable lead-receiver 34. The lead-reciever receives the pulses from outside the body. The "head" or proximal end 49 of the lead-receiver 34 (shown schematically in FIG. 9) contains the secondary coil 48 and electronic circuitry (hybrid) 167 which is hermetically sealed, and covered with silicone. It also has four anchoring sleeves 130 for tying it to the subcutaneous tissue.

The fabrication of the lead-receiver 34 is designed to be modular. Thus, several different components can be mixed and matched without altering the functionality of the device significantly. As shown in FIG. 8, the lead-receiver 34 components are the proximal end 49 (containing coil 48, electrical circuitry 167, and case 78), and distal end containing electrode 61 (cathode) & electrode 62 (anode). In the modular design concept, several design variables are possible, as shown in the table below, and described further in U.S. Pat. No. 6,205,359, which is incorporated here by reference.

frequencies away from the resonant frequency. The pulse signal from secondary (implanted) coil 48 is rectified by the diode bridge 154 and frequency reduction obtained by capacitor 158 and resistor 164. The last component in line, capacitor 166 is used for isolating the output signal from the electrode wire. The return path of signal from cathode 61 will be through anode 62 placed in proximity to the cathode 61 for "Bipolar" stimulation. In the current embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation and is therefore, used in the current embodiment. Unipolar stimulation is more likely to stimulate skeletal muscle in addition to nerve stimulation. The implanted circuit 167 in this embodiment is passive, so a battery does not have to be implanted. It is however, possible to implant a battery source for use of active component logic in the implant.

Figure 10:
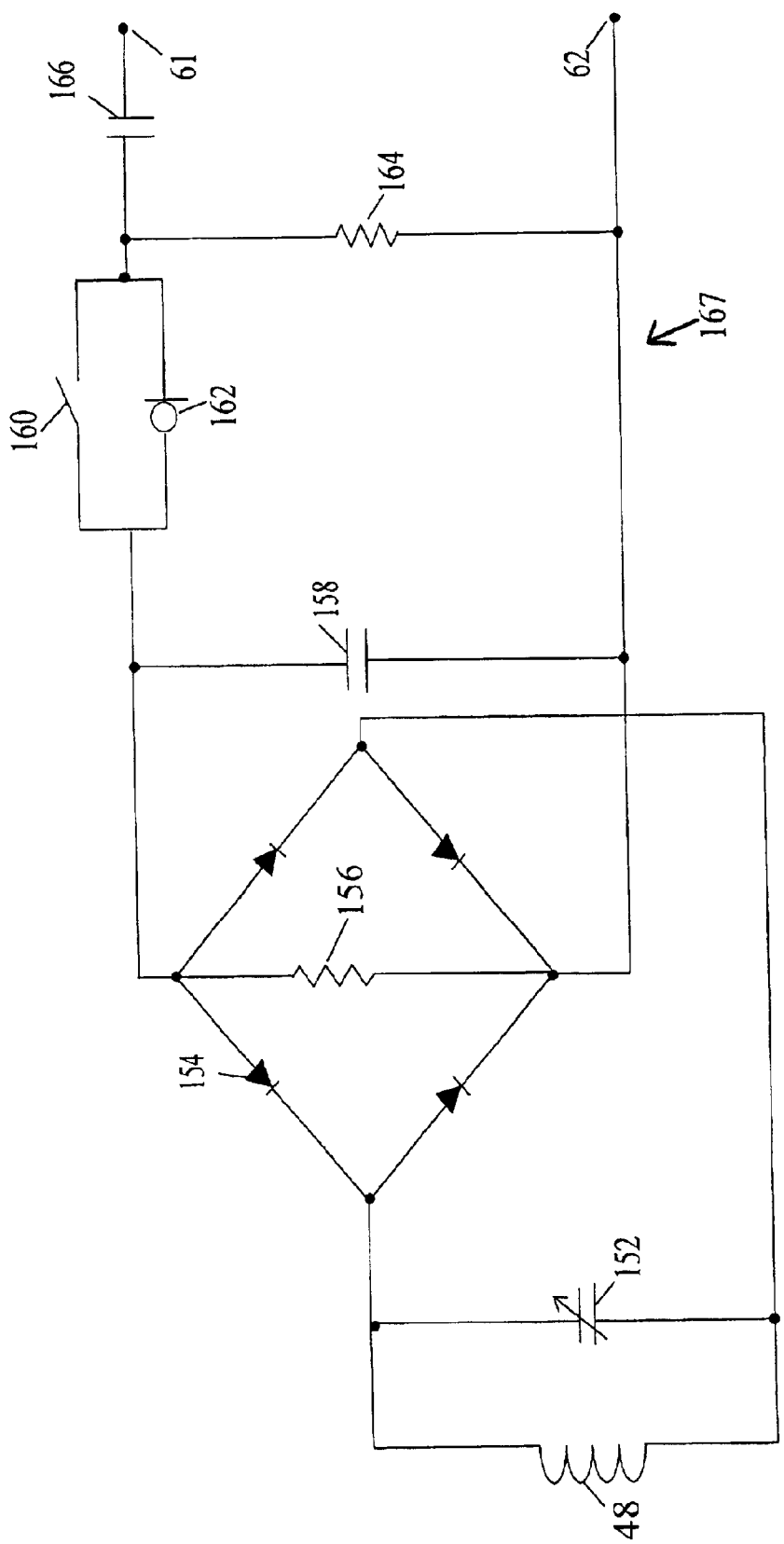
FIG. 10A is a diagram of circuitry within the proximal portion of the implanted lead-receiver.
FIG. 10B is a diagram of alternative circuitry within the proximal portion of the implanted lead-receiver.
FIG. 10C is a diagram of alternative circuitry within the proximal portion of the implanted lead-receiver.

The circuitry shown in FIGS. 10B and 10C can be used as an alternative for the implanted lead-receiver. The circuitry of FIG. 10B is a slightly simpler version, and circuitry of FIG. 10C contains a conventional NPN transistor 168 connected in an emitter-follower configuration. The circuit components are soldered in a conventional manner to an upper conductive layer on a printed circuit board.

Figure 11:
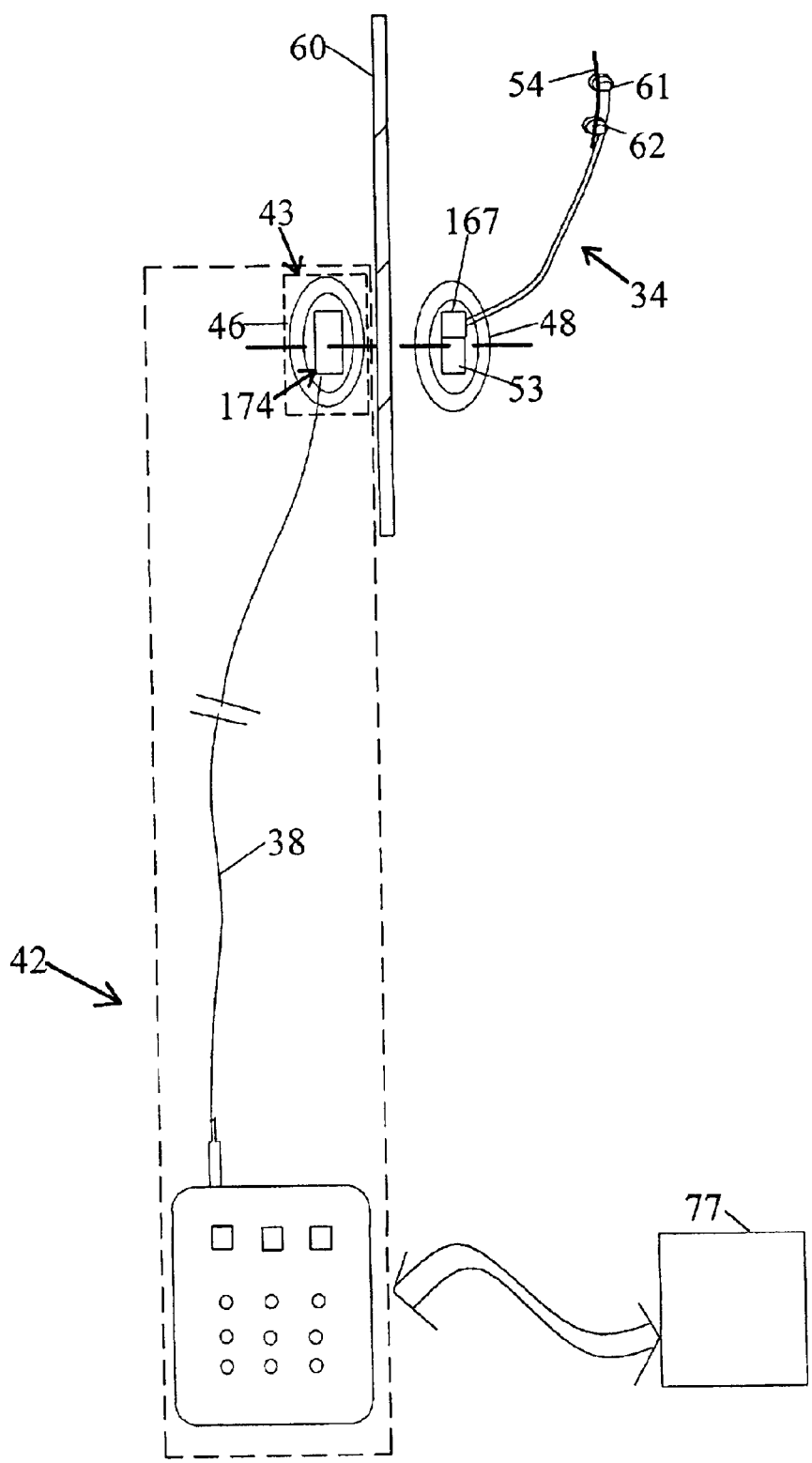
FIG. 11 is a schematic diagram of an external patch and external pulse generator.

An external patch 43 for inductive coupling is shown in FIG. 11. One end of the patch contains the coil 46, and the Table of lead-receiver design variables

| Proximal End Circuitry and Return electrode | Lead body-Lumens | Lead body-Insulation materials | Lead-Coating | Conductor (connecting proximal and distal ends) | Electrode - Material | Distal End Electrode - Type |
|---|---|---|---|---|---|---|
| Bipolar | Single | Polyurethane | Lubricious (PVP) | Alloy of Nickel-Cobalt | Pure Platinum | Standard ball electrode |
| Unipolar | Double | Silicone | Antimicrobial | | Platinum-Iridium (Pt/Ir) alloy | Hydrogel electrode |
| | Triple | Silicone with Polytetrafluoroethylene (PTFE) | Anti-inflammatory | | Pt/Ir coated with Titanium Nitride | Spiral electrode |
| | Coaxial | | | | Carbon | Steroid eluting Fiber electrode |

FIG. 9 is a close-up view of the proximal portion 49 of the lead-receiver 34 containing the circuitry (hybrid) 167. This circuitry is shown schematically in FIG. 10A. Approximately 15–25 turn copper wire of 30 gauge, or comparable thickness, is used for the primary coil 46 and secondary coil 48. This wire is concentrically wound with the windings all in one plane. The frequency of the pulse-waveform delivered to the implanted coil 48 can vary and so a variable capacitor 152 provides ability to tune secondary implanted circuit 167 to the signal from the primary coil 46. The capacitor 152 increases the sensitivity and selectivity of the receiver 34, which is made sensitive to frequencies near the resonant frequency of the tuned circuit and less sensitive to other end is fitted to the external stimulator 42. The external patch 43, is a modification of the patch available from TruMed Technologies, Burnsville, Minn. The patch 43 can be taped next to the skin 60 or, in another embodiment, slipped in the pocket of a garment in close proximity to the implanted coil 48.

Figure 12:
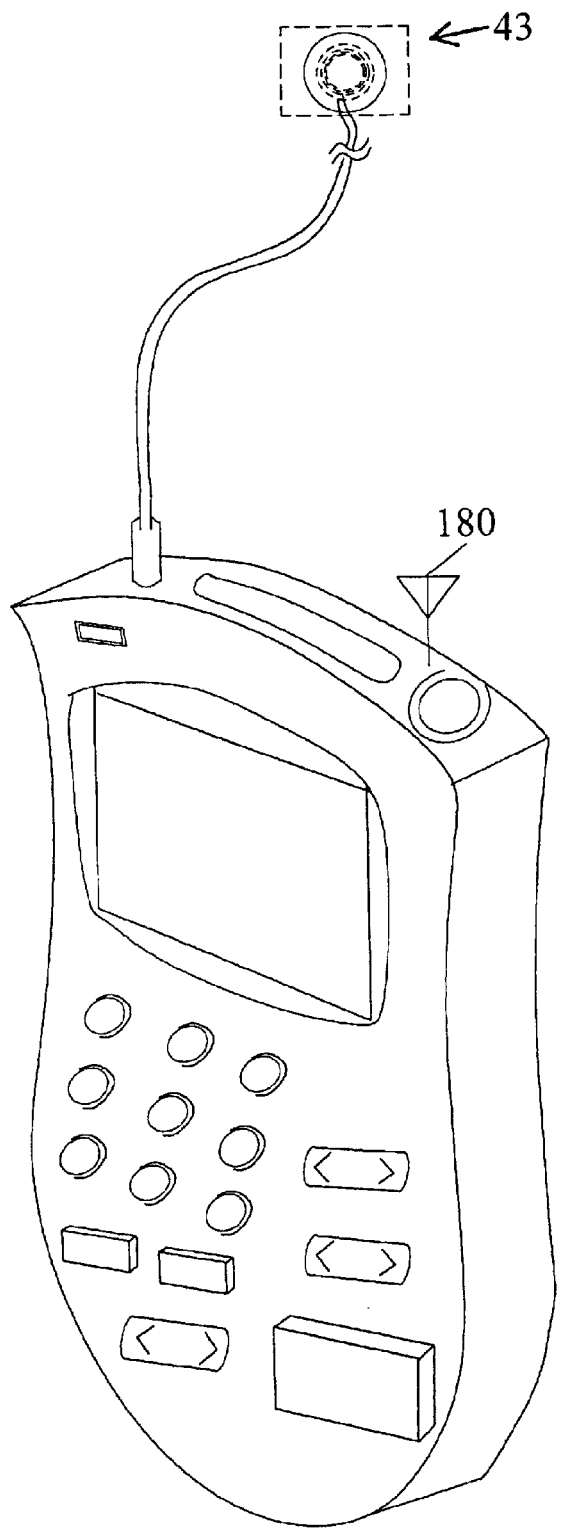
FIG. 12 is a prospective view of an external pulse generator.

FIG. 12 shows a front view of an external stimulator 42. The external stimulator 42 contains the circuitry, rechargeable power source, external coil and an optional telemetry module. The external stimulator 42 has two modes of operation. In the first mode of operation there are a limited number of pre-determined programs. The number of programs can be any reasonable number of programs. Any number of pre-determined programs up to 100 programs are considered within the scope of the invention. For patient convenience, the presently preferred embodiment contains less than twenty predetermined programs.

These programs differ in stimulus intensity, pulse width, frequency of stimulation, and on-off timing sequence, e.g. "on" for 10 seconds and "off" for 50 seconds in repeating cycles. For patient safety, any number of these programs may be locked-out by the manufacturer or the physician.

Pre-determined programs contain programs ranging from least aggressive therapy programs to most aggressive therapy.

The following are illustrative examples of mild to aggressive therapy programs,

Program #1:
   1.0 mA current output, 0.2 msec pulse width, 15 Hz pulse frequency, 15 sec ON time-1.0 min OFF time, in repeating cycles.

Program #2:
   1.5 mA current output, 0.3 msec pulse width, 20 Hz pulse frequency, 20 sec ON time-2.0 min OFF time, in repeating cycles.

Program #5:
   2.0 mA current output, 0.2 msec pulse width, 25 Hz pulse frequency, 20 sec ON time-1.0 min OFF time, in repeating cycles.

Program #6:
   2.0 mA current output, 0.25 msec pulse width, 25 Hz pulse frequency, 30 sec ON time-1.0 min OFF time, in repeating cycles.

Program #8:
   2.5 mA current output, 0.3 msec pulse width, 30 Hz pulse frequency, 40 sec ON time-1.5 min OFF time, in repeating cycles.

Program #9:
   3.0 mA current output, 0.4 msec pulse width, 30 Hz pulse frequency, 30 sec ON time-1.0 min OFF time, in repeating cycles.

The majority of patients will fall into the category that require an intermediate level of therapy, such as program #5. In the above examples of pre-determined programs, the parameters of output is what is delivered to the nerve. It being understood that the actual parameters may deviate somewhat from these. Additionally, the parameters for anxiety disorders may be different than for obesity disorders.

In a second mode of operation, the individual parameters such as stimulus amplitude, pulse width, frequency of stimulation (pulses/sec), on-time, and off-time sequence can be adjusted individually and locked into a "custom" program by the physician, and stored in the memory. In the presently preferred embodiment the programmable range of parameters are:

| PARAMETER | RANGE |
| --- | --- |
| Voltage | 1 volt to 50 volts (peak-to-peak) |
| Pulse width | 0.05 millisec. to 4.0 millisec. |
| Pulses per second | 5 Hz to 200 Hz |
| Stimulation on-time | 1 sec. to 24 hrs. |
| Stimutation off-time | 1 sec. to 24 hrs. |

When the device is turned on, a green light emitting diode (LED) indicates that the device is emitting electrical stimulation.

Figure 13:
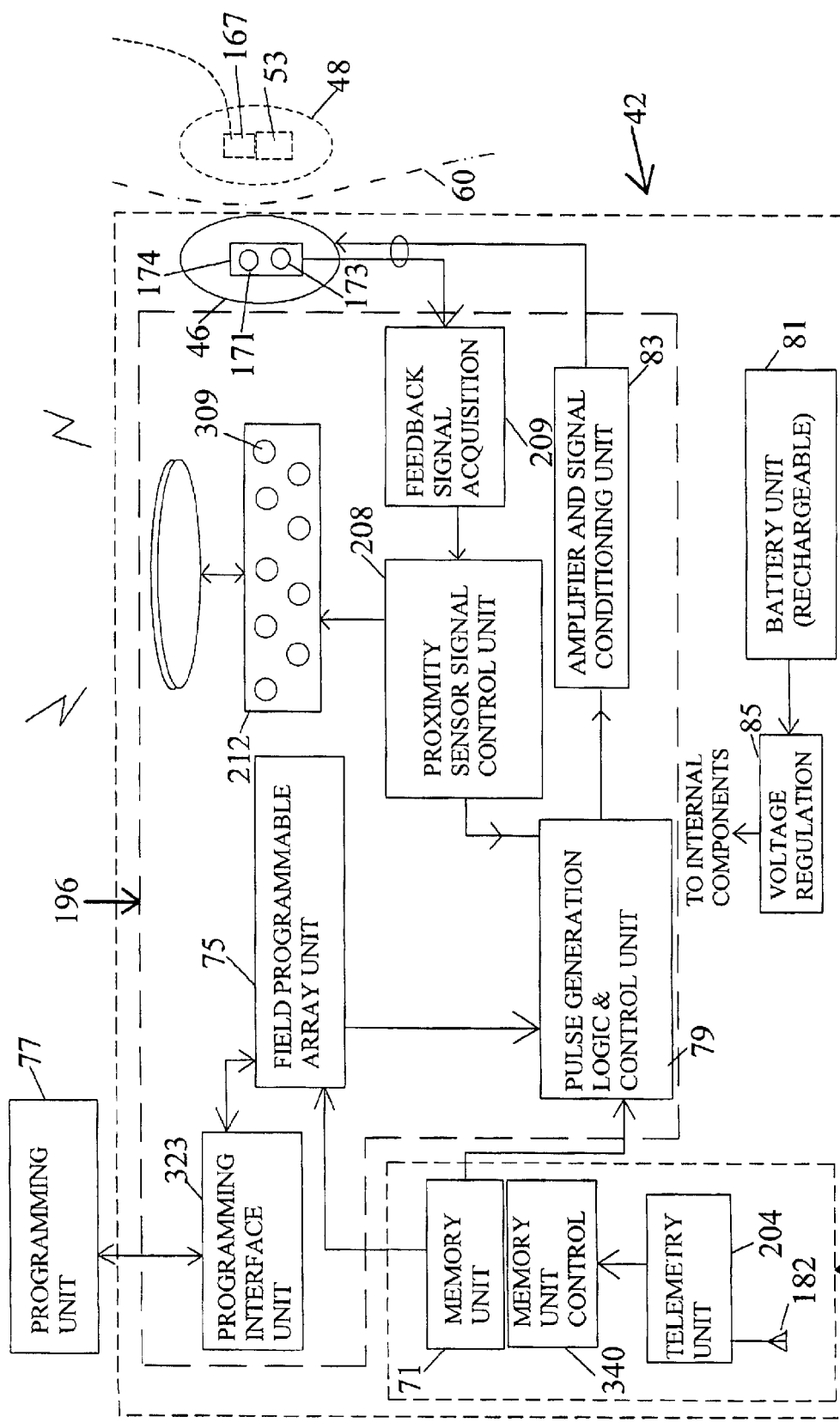
FIG. 13A is a block diagram of the external stimulator and lead reciever.
FIG. 13B is a block diagram of programmable array logic interfaced to the programming station.
FIG. 13C is a block diagram showing details of programmable logic array unit.
FIG. 13D diagram showing details of the interface between the programmable array logic and interface unit.
FIG. 13E is a diagram showing the circuitry of the pulse generator
Figure 13:
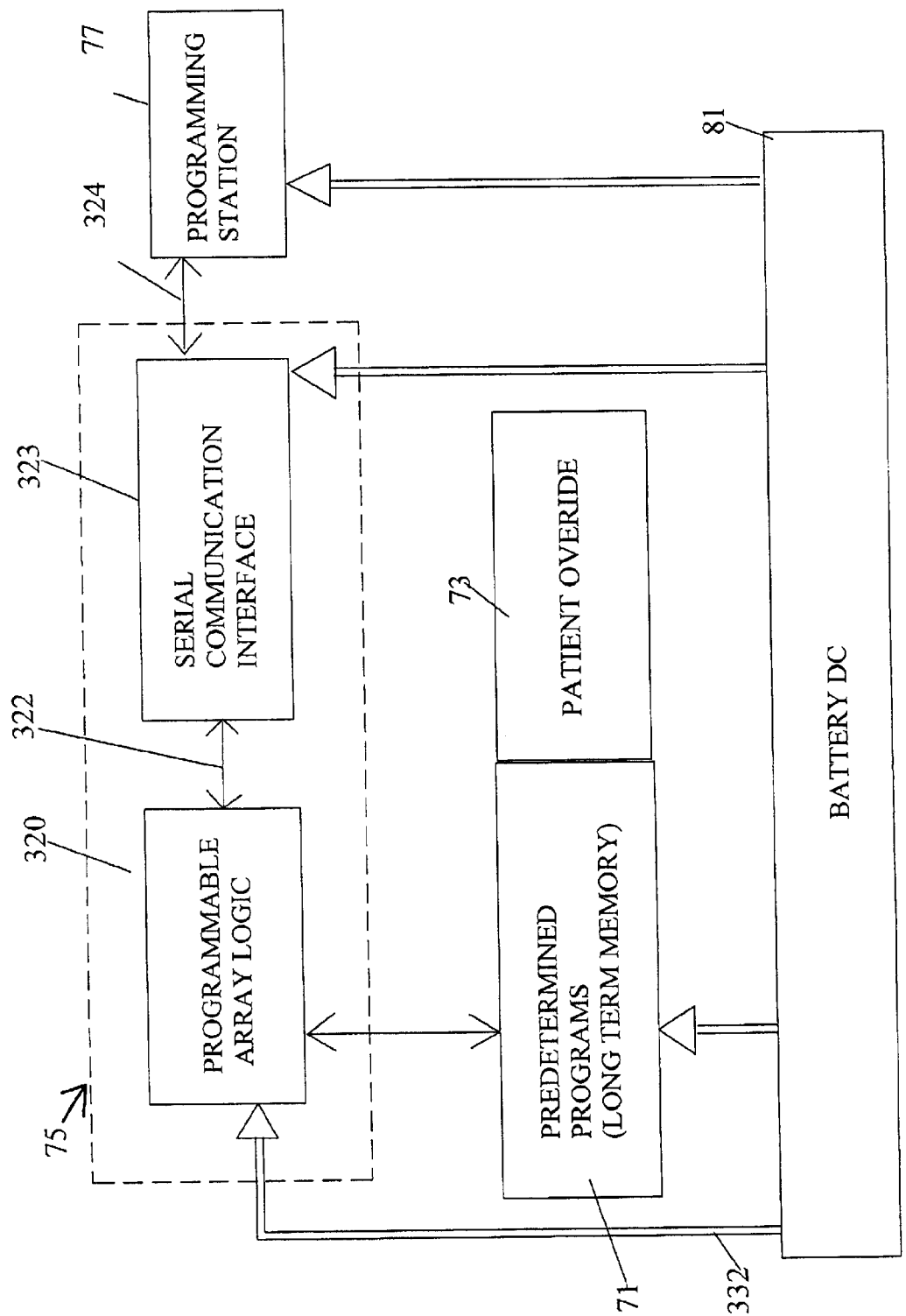
Figure 13:
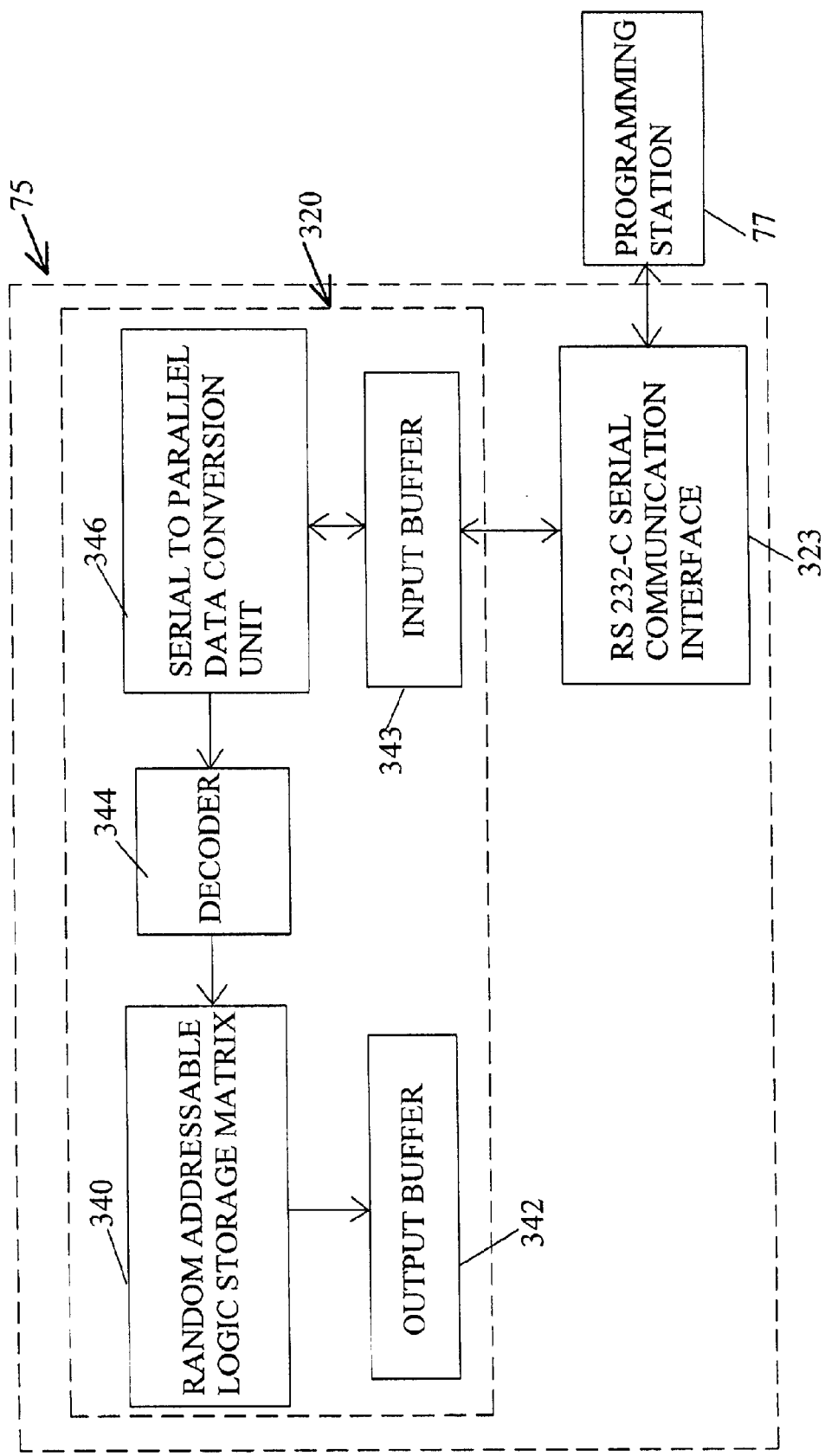
Figure 13:
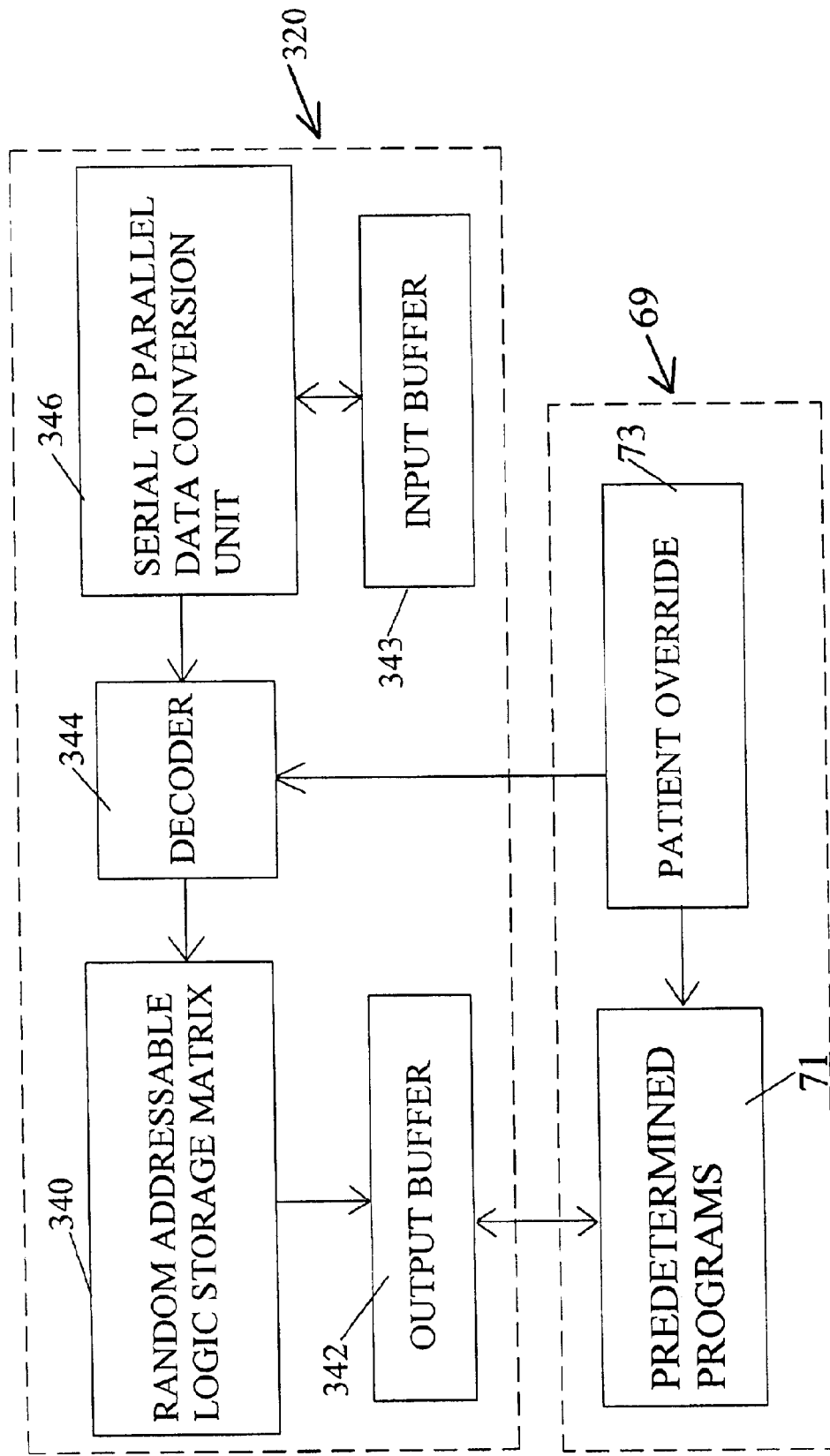
Figure 13:
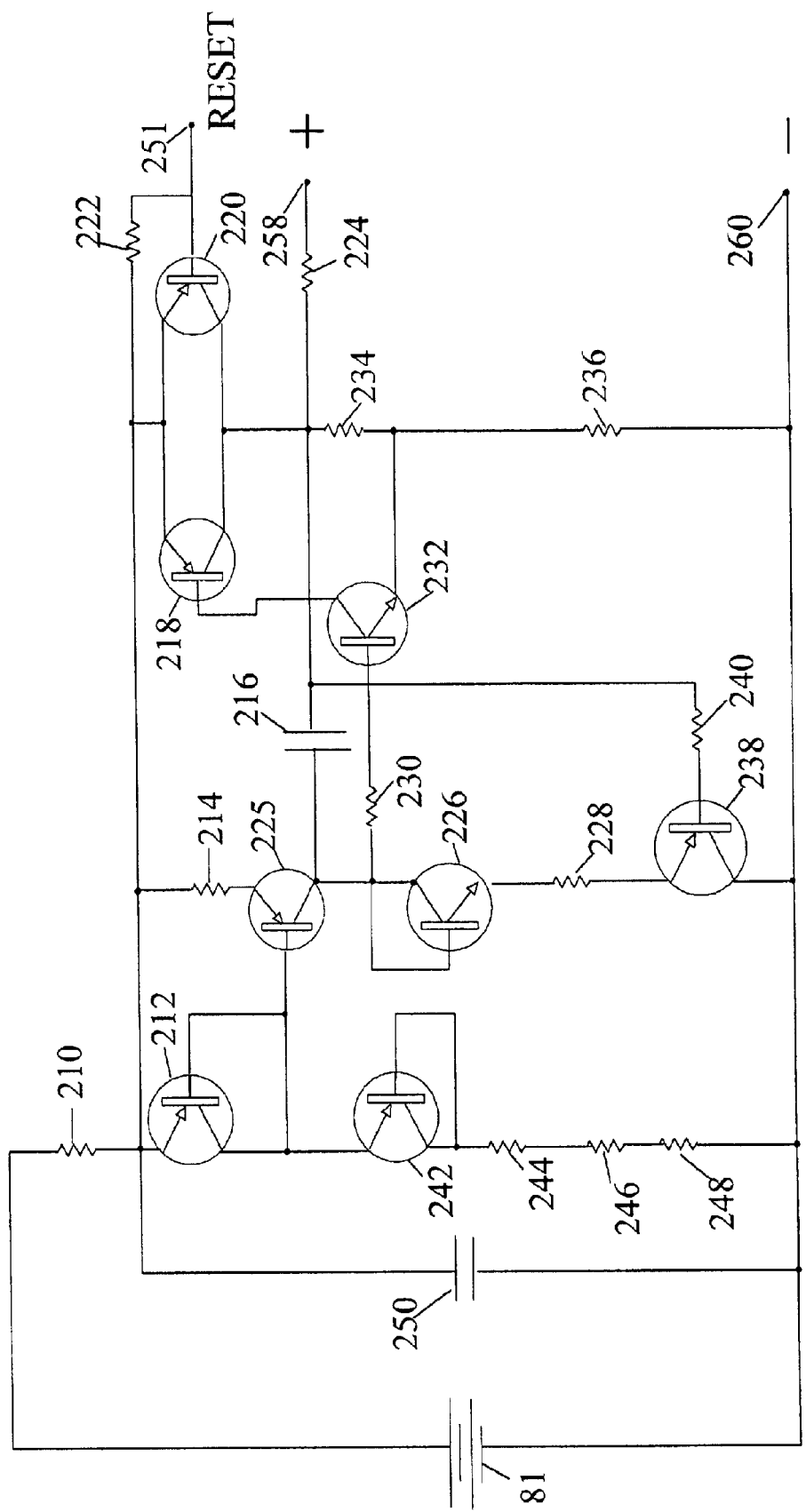

FIG. 13A shows a block diagram of the external stimulator 42. The pre-packaged programs are stored in the memory unit 71. This represents memory with a readable and writeable portion and a non-volatile pre-programmable portion. A Field Programmable Array Unit (FPGA) 75 and a random access component (RAM) 320 and Random addressable storage logic 340, facilitates application of logic to edit and change the "current" parameters being utilized for pulse generation. The programmable unit interface 323 provides an interface to a programming unit (portable computer system) 77, which allows re-loading of a new set of predetermined programs. The pulse generation component 79 generates pulses of well-defined parameters, selected from the programmed parameters that exist in the memory unit 71. The pulse signal generation unit 79 provides its signal to be amplified and conditioned at the amplifier and signal conditioning unit 83 which then provides these signals to the primary (external) inductive coil 46. In one embodiment a pair of sensors 174 senses the position of the implanted magnet 53 and the sensor signal is fed back to the proximity sensor control block 208 via the feedback signal conditioning unit 209. The feedback signal provides a proportional signal for modification of the frequency, amplitude and pulse-width of the pulse being generated by the pulse signal generator unit 79. The sensor unit has two sensors 171, 173 that sense the location of the implanted magnet 53. The implanted (secondary) coil 48 is rigidly connected to the passive circuit and magnet 53. The skin 60 separates the subcutaneous and external components. The external components are placed on the skin, with the primary coil 46 in close proximity and optimally situated with respect to the implanted (secondary) coil 48.

Figure 15:
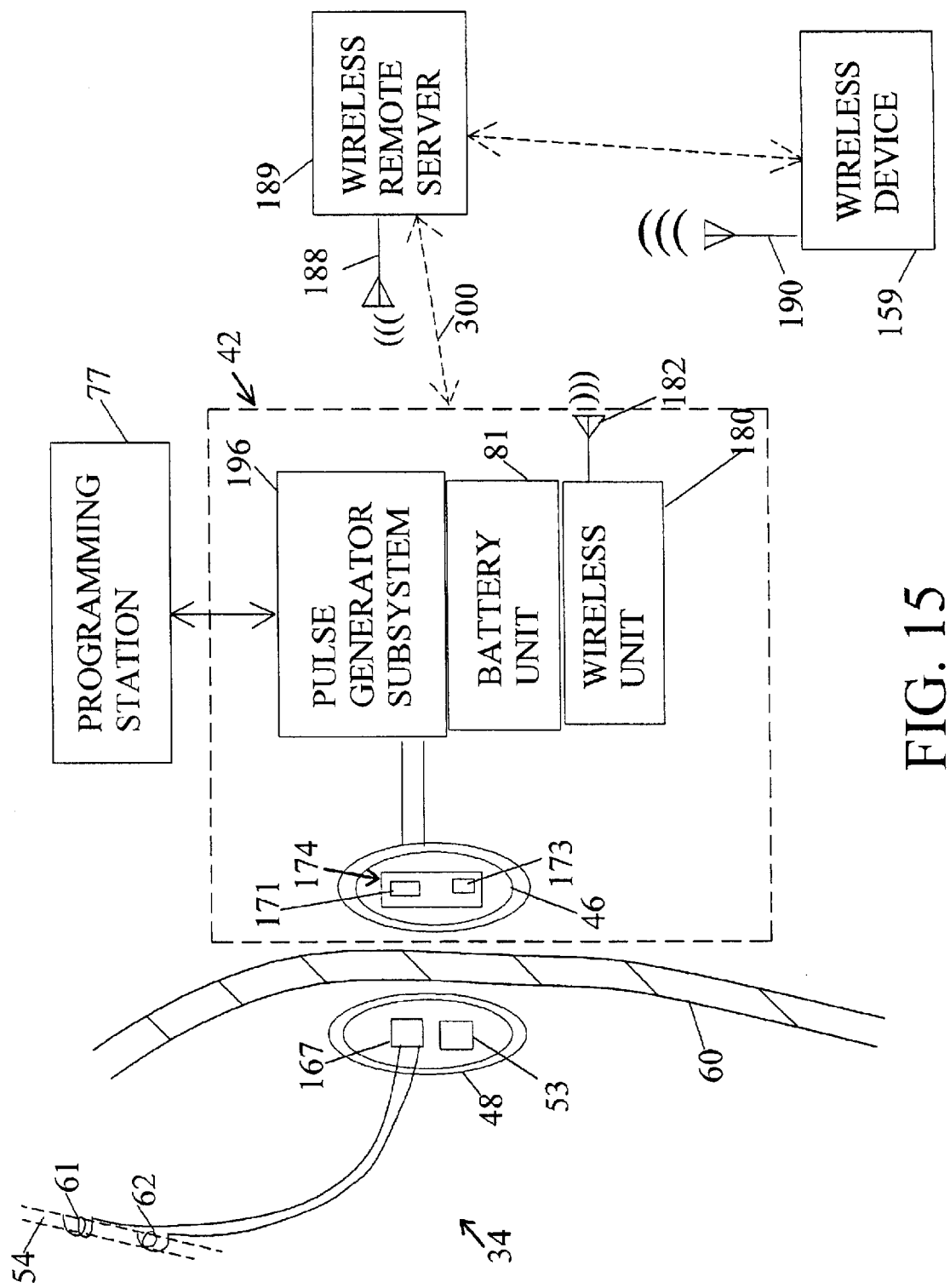
FIG. 15 is a schematic diagram of the pulse generator and two-way communication through a server.

As shown in FIG. 13A and FIG. 15, the external pulse generator 42 is composed of three modules or sub-assemblies. The first sub-assembly is the pulse generation and signal conditioning components 196, the second is the battery 81, and the third is the telemetry and memory unit 180. The presently preffered embodiment, comprises proximity sensing and feedback circuitry. The pulse generator is able to function as supplier of electric pulses to the nerve tissue without the proximity feedback loop and the telemetry module. These modules or sub-assemblies also provide for a scalable external pulse generator 42. In the telemetry module, a wireless antenna 182 provides a means of communication to the external pulse generator 42 and the wireless remote server 189. A programming unit 77 can be physically connected to the stimulator 42 (via the Programming Unit Interface 323) in a tethered manner for loading of new predetermined programs or changing parameters of an existing program.

FIG. 13B shows the Programmable Array Logic and Interface Unit 75 interfaced to the Programming Station 77. The programming station allows the user to change the program parameters for various stimulation programs. The programming station is connected to the Programmable Array Unit 75 with an RS232-C serial connection 324. The main purpose of the serial line interface is to provide an RS232-C standard interface. This method enables any portable computer with a serial interface to communicate and program the parameters for storing the various programs. The serial communication interface 323 receives the serial data, buffers this data and converts it to a 16 bit parallel data. The Programmable Array Logic 320 component of Programmable Array Unit 75 receives the parallel data bus and stores or modifies the data into a random access matrix. This array of data also contains special logic and instructions along with the actual data. These special instructions also provide an algorithm for storing, updating and retrieving the parameters from long-term memory. The Programmable Array Unit 320, interfaces with Long Term Memory 71 to store the pre-determined programs. All the previously modified programs can be stored here for access at any time. The programs will consist of specific parameters and each unique program will be stored sequentially in Long Term Memory 71. A battery unit 81 provides power to all the components shown above. The logic for the storage and decoding is stored in the Random Addressable Storage Matrix (RASM) 340 (FIG. 13C).

FIG. 13C shows greater details for the Programmable Logic Array Unit 320. The Input Buffer block 343 stores the serial data in temporary register storage. This accumulation allows for the serial to parallel conversion to occur. The serial to 16 bit parallel block sets up 16 bits of data 346, as created from the RS232-C serial data. This parallel data bus will communicate the data and the address information. The decoder block 344 decodes address information for the Random Addressable Logic Storage Matrix 340 from which to access the data i.e. programmer parameters. The Output Buffer 342 provides an interface to the Long Term Memory 71.

FIG. 13D shows schematically the details of the interface between the Programmable Array Logic 320 and Interface Unit 75 which is connected to the Predetermined Programs block (Long Term Memory) 71. The Patient Override 73 is essentially a control scheme for initializing or starting a program at any intermediate point. The Field Programmable array provides a reconfigurable mechanism to store data and associated instructions for the programs. It supports adding, modifying or retrieving the data from a Random Addressable Logic Storage Matrix 340. This is also a scheme for treating "flexible" logic description and control. It is flexible by providing the ability to reprogram and even redesign existing programs previously installed as predetermined programs. As was shown schematically in FIG. 13A, the health care provider can load and reload stimulation programs of choice. This allows the authorized user to create, modify and select for execution, programs to use for a particular time period.

Moving now to the pulse generator circuitry, shown schematically in FIG. 13E, which exhibits typical multivibrator functionality. This circuit produces regularly occurring pulses where the amplitude, pulse width and frequency is adjustable. The battery 81 is the main external power source for this circuit. The capacitor 250 is connected in parallel with the battery 81. The combination of transistors 212, 242 and 225, and resistors 210, 244, 246 and 248 acts as a constant current source generated at the collector of transistor 226. The transistor 212 has collector connected to the emitter of transistor 242 and base of transistor 225. The transistors 212 and 242 are connected to provide a constant voltage drop. Likewise, transistor 226 also acts as a diode with a resistor 228 connected in series and further connected to the negative terminal of the line at terminal 260. Capacitor 216 provides timing characteristics and its value helps determine pulse width and pulse frequency. The output of the oscillator appears at terminal 258.

Initially, the capacitor 216 gets charged with current from the path of resistor 234 and 236 while all the transistors are turned off. As the capacitor charges up transistor 232 will become forward biased and current will flow via resistors 230 and 236 from the base to emitter resistors. This action turns on the transistor 218 and the positive voltage from the power supply 81 is made available at the base of transistor 238 through resistor 240. This results in the transistor 238 getting turned on. The conduction of transistor 238 causes capacitor 216 to discharge. The time constant for the charge and discharge of capacitor 216 is determined by value of the resistors 228 and 240 and capacitor 216. After the time constant, transistor 232 turns off, and this in turn turns off transistors 238 and 218. A reset mechanism for this multivibrator can be provided by setting a positive voltage, for example 2.5 volts, to the base of transistor 220. This positive increase in voltage turns on transistor 220 followed by transistor 238. The turning on of transistor 238 discharges the capacitor 216 and the reset operation is complete.

Conventional integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver these pre-determined programs is well known to those skilled in the art.

Figure 14:
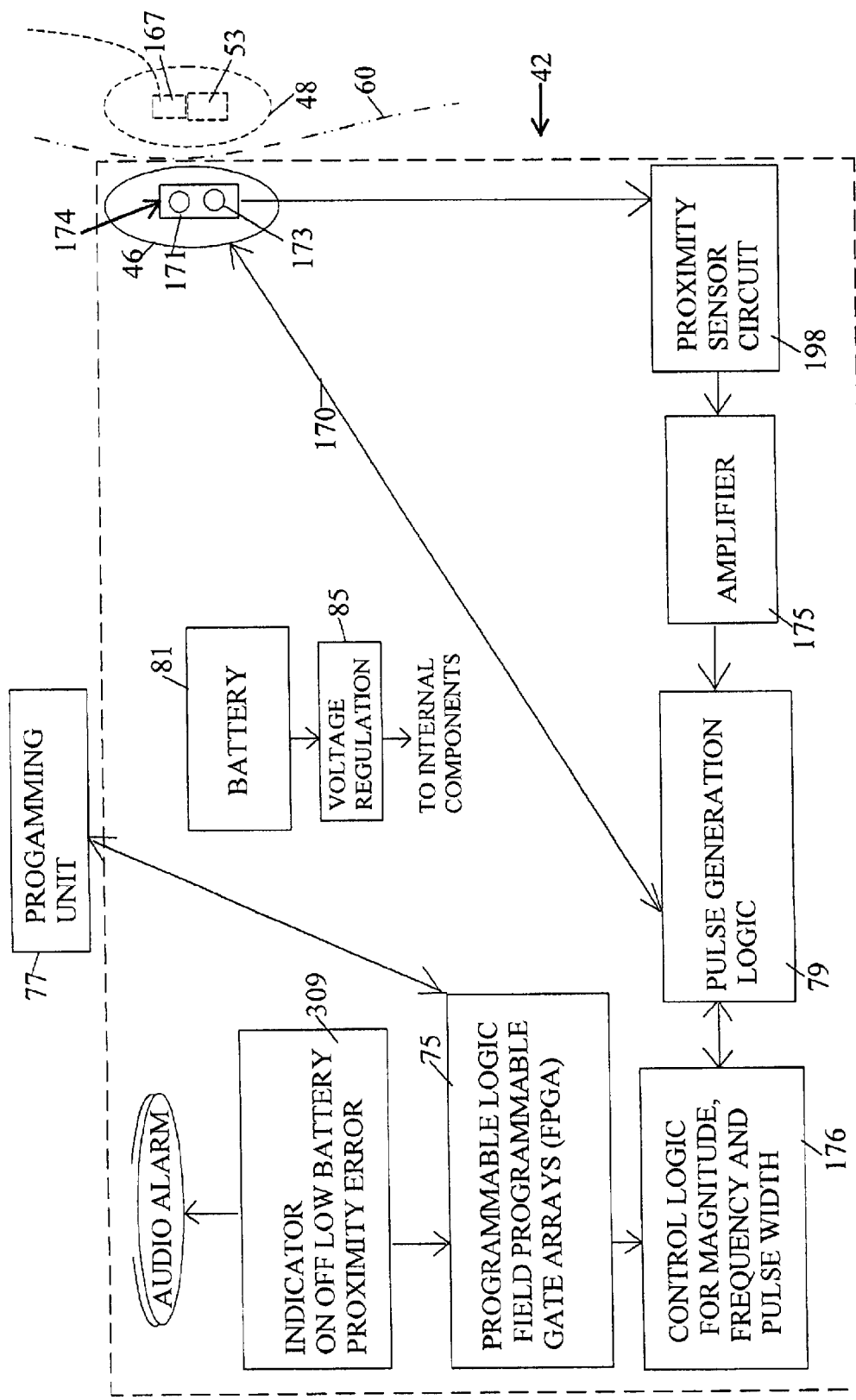
FIG. 14 is a block diagram showing the proximity sensing and feedback regulation part in the pulse generator.

FIG. 14 shows an overall block diagram of the proximity sensing and feedback regulation in the current embodiment, even though other methods of proximity sensing can be used. In the presently preferred method incorporates an external coil 46, a proximity sensing unit 174, and a subcutaneous secondary coil 48 with a GMR magnet 53 associated with the proximity sensing unit 174. A proximity sensing circuit 198 provides feedback of the position of the implanted secondary coil 48. The signal output from proximity sensing circuit 198 is derived from the relative location of the coils 46 and 48. The coil sub-assemblies consist of the coil and the associated electronic components that are rigidly connected to the respective coil. The signal from the proximity sensing circuit 198 is provided to the pulse generation logic 79 through amplifier 175 and this signal varies to compensate for any variation of the nominal signal from proximity sensing circuit 198. The programmable parameters are stored in a programmable logic 320. These parameters are provided to the control logic 75, for pulse amplitude and pulse-width control. The battery (rechargeable) 81 provides power to all other devices such as the control logic for pulse amplitude and pulse width, the pulse generation logic 79, the differential amplifier 175, the proximity sensing circuit 198, the programmable logic 75, the proximity sensing unit 174 and the indicator unit 309. The output of the pulse generation logic 79 is provided to the external coil 46 as indicated by arrow 170. The sensor and associated circuit present in the proximity sensing unit 174 is located partially in the external stimulator 42.

In one embodiment of the invention the external pulse generator 42 has two-way wireless communication capabilities with a remote server, using a communication protocol such as the wireless application protocol (WAP). The purpose of the telemetry module is to enable the physician to remotely, via the wireless medium change the programs, activate, or disengage programs. Additionally, schedules of therapy programs, can be remotely transmitted and verified. The physicians are thus able to remotely control the stimulation therapy.

FIG. 15 is a simplified schematic showing the communication aspects between the pulse generator 42 and the remote hand-held computer. A desktop or laptop computer can be a server 189 which is situated remotely, perhaps at a health-care provider's facility or a hospital. The data can be viewed at this facility or reviewed remotely by medical personnel on a wireless internet supported hand-held device 159, which could be a personal data assistant (PDA), for example, a "palm-pilot" from PALM corp. (Santa Clara, Calif.), a "Visor" from Handspring Corp. (Mountain view, CA) or on a personal computer (PC) available from numerous vendors or a cell phone or a handheld device being a combination thereof. The physician or appropriate medical personnel, is able to interrogate the external stimulator 42 device and know what the device is currently programmed to, as well as, get a graphical display of the pulse train. The wireless communication with the remote server 189 and hand-held device (wireless internet supported) 159 can be achieved in all geographical locations within and outside the United States (US) that provides cell phone voice and data communication service. The pulse generation parameter data can also be viewed on the handheld devices 159.

The telecommunications component of this invention uses Wireless Application Protocol (WAP). WAP is a set of communication protocols standardizing Internet access for wireless devices. Previously, manufacturers used different technologies to get Internet on hand-held devices. With WAP, devices and services inter-operate. WAP promotes convergence of wireless data and the Internet. The WAP Layers are Wireless Application Envirnment (WAEW), Wireless Session Layer (WSL), Wireless Transport Layer Security (WTLS) and Wireless Transport Layer (WTP).

Figure 16:
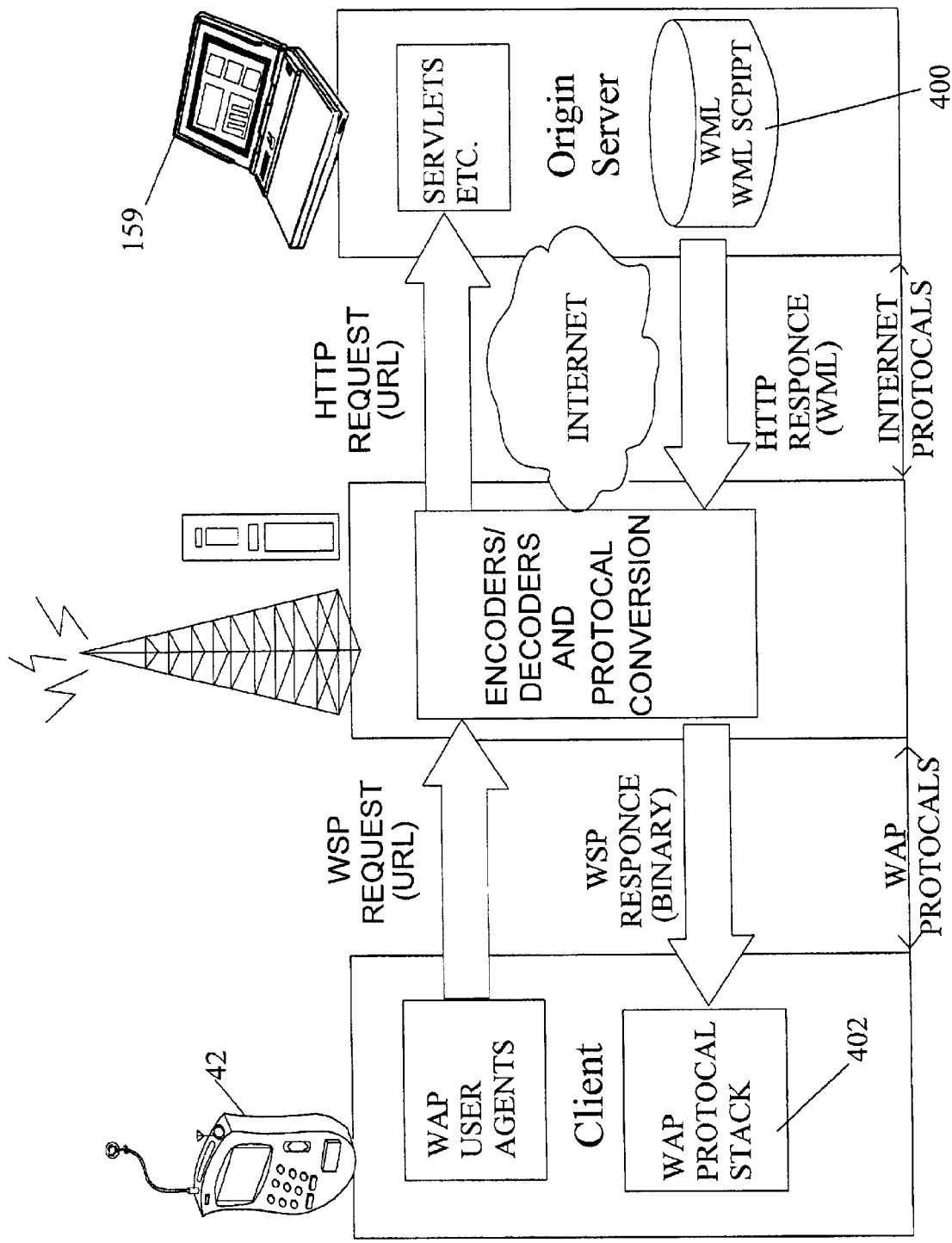
FIG. 16 is a schematic diagram of the wireless protocol.

The WAP programming model, which is heavily based on the existing Internet programming model, is shown schematically in FIG. 16. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops. Such features are facilitated with WAP.

The key components of the WAP technology, as shown in FIG. 16, includes 1) Wireless Mark-up Language (WML) 400 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/WMLScript content. 4) A lightweight protocol stack 402 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support header caching, thereby economizing on bandwidth requirements. WSP also compensates for high latency by allowing requests and responses to be handles asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications, and well known to those skilled in the art.

The presently preferred embodiment utilizes WAP, because WAP has the following advantages, 1) WAP protocol uses less than one-half the number of packets that the standard HTTP or TCP/IP Internet stack uses to deliver the same content. 2) Addressing the limited resources of the terminal, the browser, and the lightweight protocol stack are designed to make small claims on CPU and ROM. 3) Binary encoding of WML and SMLScript helps keep the RAM as small as possible. And, 4) Keeping the bearer utilization low takes account of the limited battery power of the terminal.

In this embodiment two modes of communication are possible. In the first, the server initiates an upload of the actual parameters being applied to the patient, receives these from the stimulator, and stores these in its memory, accessible to the authorized user as a dedicated content driven web page. The web page is managed with adequate security and password protection. The physician or authorized user can make alterations to the actual parameters, as available on the server, and then initiate a communication session with the stimulator device to download these parameters.

The physician is also able to set up long-term schedules of stimulation therapy for their patient population, through wireless communication with the server. The server in turn communicates these programs to the neurostimulator. For instance, a physician may program an Alzheimer's patient to a stimulation program for two weeks, and program an epilepsy patient to a selected long-term "on", "off" stimulation therapy. Each schedule is securely maintained on the server, and is editable by the physician and can get uploaded to the patient's stimulator device at a scheduled time. Thus, therapy can be customized for each individual patient. Each device issued to a patient has a unique identification key in order to guarantee secure communication between the wireless server 189 and stimulator device 42.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. An external electrical stimulator for providing electrical pulses for treatment of obesity, eating disorders, anxiety disorders and obsessive compulsive disorders, comprising:
   a) a power source, primary coil and circuitry to provide electrical pulses;
   b) at least two predetermined programs to control said electric pulses generated by said external electrical stimulator; and
   c) proximity sensing and feedback regulation means to regulate said electrical pulses,
   whereby said electrical pulses are provided for treating or alleviating symptoms of said disorders.

2. The stimulator of claim 1, wherein said electrical pulses comprises pulsed electrical stimulation to the vagus nerve.

3. The stimulator of claim 2, wherein said electric pulses to said vagus nerve are provided at levels ranging from the neck to the stomach.

4. The stimulator of claim 1, wherein said electrical pulses comprise at least one variable component selected from the group consisting of pulse amplitude, pulse width, pulses per second, on-time and off-time, which can be individually selected and programmed.

5. The stimulator of claim 4, wherein said pulse width ranges from 0.05 milliseconds to 4.0 milliseconds.

6. The stimulator of claim 4, wherein said pulses per second ranges from 5 Hz to 200 Hz.

7. The stimulator of claim 4, wherein
   a) said on-time ranges from 1 second to 24 hours, and
   b) said off-time can range from 1 second to 24 hours.

8. The stimulator of claim 1, wherein further comprising wireless telemetry means to remotely control said electrical pulses.

9. The stimulator of claim 1, wherein said predetermined programs comprises unique combinations of pulse amplitude, pulse width, pulse frequency, and on-off times.

10. An external pulse generator for providing neuromodulation therapy for obesity, eating disorders, anxiety disorders and obsessive compulsive disorders, comprising:
- a) a power source, primary coil and circuitry to emit electrical signals, and
- b) at least two predetermined programs to control said electric signals, and wherein said external pulse generator is adapted to be inductively coupled with an implanted receiving means which is in electrical contact with the nerve tissue; and
- c) proximity sensing and feedback regulation means to regulate said electrical signals, whereby said electrical signals are provided for said neuromodulation therapy.

11. The pulse generator of claim 10, wherein said neuromodulation therapy comprises pulsed electrical stimulation to the vague nerve.

12. The pulse generator of claim 10, wherein said electric signals to said vagus nerve are provided at selective levels between the neck and the stomach.

13. The pulse generator of claim 10, wherein said predetermined programs comprises unique combinations of pulse amplitude, pulse width, pulse frequency, and on-off times.

14. The pulse generator of claim 10, wherein said pre-determined programs are capable of being modified to modify sold electrical signal.

15. The pulse generator of claim 10, wherein at least one said pre-determined program is locked out to the patient.

16. The pulse generator of claim 10, wherein said electrical signals comprise at least one variable component selected from the group consisting of pulse amplitude, pulse width, pulses per second, on-time and off-time, such that each value of said variables can be individually selected and programmed.

17. The pulse generator of claim 16, wherein said pulse amplitude emitted by primary coil ranges from 1 volt to 50 volts peak-to-peak.

18. The pulse generator of claim 16, wherein pulse width ranges from 0.05 milliseconds to 4.0 milliseconds.

19. The pulse generator of claim 16, wherein said electrical pulses per second ranges from 5 Hz to 200 Hz.

20. The pulse generator of claim 16, wherein
- a) stimulation on-time ranges from 1 second to 24 hours, and
- b) stimulation off-time ranges from 1 second to 24 hours.

21. The pulse generator of claim 10, wherein said programs can be stored in memory.

22. The pulse generator of claim 10, further comprising a wireless telemetry means to remotely control said neuromodulation therapy.

23. An external pulse generator, adapted to be inductively coupled with an implanted receiving means which is in electrical contact with nerve tissue, for providing electrical signals to provide therapy for at least one of obesity, eating disorders, neurologic, neuropsychiatric, and urological disorders comprising:
- a) a power source, primary coil, and circuitry to provide electrical signals,
- b) at least two predetermined programs to control said electric signals,
- c) proximity sensing and feedback regulation means to regulate said electrical signals; and
- d) wireless telemetry means for remote communication, whereby said electric signals provided by said external pulse generator can be wirelessly remote controlled.

24. The external pulse generator of claim 23, wherein said predetermined programs consist of unique combination of pulse width, pulse amplitude, pulse/second, on-time and off time.

25. The pulse generator of claim 23, wherein said pre-determined programs are capable of being modified to modify said electrical signal.

26. The pulse generator of claim 23, wherein at least one of said pre-determined program is locked out to the patient.

27. The pulse generator of claim 23, wherein at least one of said pre-determined program is not locked out to the patient.

28. The external pulse generator of claim 23, wherein said electrical signals comprise at least one variable component selected from the group consisting of pulse amplitude, pulse width, pulses per second, on-time and off-time, which can be individually selected, programmed and stored in memory.

29. The pulse generator of claim 28, wherein said pulse amplitude of primary coil ranges from 1 volt to 60 volts peak-to-peak.

30. The pulse generator of claim 28, wherein said pulse width ranges from 0.05 milliseconds to 4.0 milliseconds.

31. The pulse generator of claim 28, wherein said pulses per second ranges from 5 pulses/sec to 200 pulses/sec.

32. The pulse generator of claim 28, wherein
- a) said on-time ranges from 1 second to 24 hours, and
- b) said off-time can range from 1 second to 24 hours.

33. An external pulse generator for providing pulsed electrical signals to vagus nerve, for treatment of obesity, eating disorders, anxiety disorders, comprising:
- a) a power source, primary coil, circuitry to provide electrical signals, and at least two predetermined programs,
- b) said external pulse generator adapted to be inductively coupled with an implanted receiving means which is in electrical contact with said vagus nerve, and
- c) proximity sensing and feedback regulation means to regulate said electrical signals.

* * * * *